US010973506B2

(12) United States Patent
Smith et al.

(10) Patent No.: US 10,973,506 B2
(45) Date of Patent: Apr. 13, 2021

(54) SYSTEMS, DEVICES, AND RELATED METHODS FOR RETRACTING TISSUE

(71) Applicant: Boston Scientific Scimed, Inc., Maple Grove, MN (US)

(72) Inventors: Paul Smith, Smithfield, RI (US); Ryan V. Wales, Northborough, MA (US); Kevin James McElwee, Franklin, MA (US); Naroun Suon, Lawrence, MA (US); Samuel Raybin, Marlborough, MA (US); Alexander Joseph Burnham, Southbury, CT (US); Ray Hewenson Tong, Foxboro, MA (US); Mary Ann Cornell, Brimfield, MA (US); Niklas Andersson, Wayland, MA (US); John B. Golden, Norton, MA (US); Scott E. Brechbiel, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 578 days.

(21) Appl. No.: 15/669,005

(22) Filed: Aug. 4, 2017

(65) Prior Publication Data
US 2018/0035997 A1 Feb. 8, 2018

Related U.S. Application Data

(60) Provisional application No. 62/371,471, filed on Aug. 5, 2016.

(51) Int. Cl.
*A61B 17/04* (2006.01)
*A61B 17/08* (2006.01)
(Continued)

(52) U.S. Cl.
CPC .... *A61B 17/0401* (2013.01); *A61B 17/00234* (2013.01); *A61B 17/0218* (2013.01);
(Continued)

(58) Field of Classification Search
CPC .......... A61B 17/00234; A61B 17/0218; A61B 17/0401; A61B 17/083; A61B 17/122;
(Continued)

(56) References Cited

U.S. PATENT DOCUMENTS 5,464,426 A * 11/1995 Bonutti .............. A61B 17/0401
606/216
5,569,274 A 10/1996 Rapacki et al.
(Continued)

FOREIGN PATENT DOCUMENTS

EP 2 308 394 A1 4/2011
JP 2008062004 A 3/2008
(Continued)

OTHER PUBLICATIONS

Sakamoto, N., et al., "Endoscopic submucosal dissection of large colorectal tumors by using a novel spring-action S-O clip for traction (with video)", Gastrointestinal Endoscopy 69(7):1370-1374 (2009).

(Continued)

*Primary Examiner* — Christine H Matthews
(74) *Attorney, Agent, or Firm* — Kacvinsky Daisak Bluni PLLC

(57) ABSTRACT

In one aspect of the present disclosure, a tissue retraction system may include a first anchor, a second anchor, and an elongate coupling member extending between the first anchor and the second anchor. The system also may include a holder for receiving the first anchor, the second anchor, and the elongate coupling element. The holder may include a proximal portion and a distal portion. The distal portion may (Continued)

have a smaller width than the proximal portion such that the distal portion exerts a force on a proximal end of the first anchor during deployment of the first anchor from the holder. The force may move the first anchor into an open configuration for receiving tissue.

19 Claims, 25 Drawing Sheets

(51) Int. Cl.
```
A61B 17/00      (2006.01)
A61B 17/02      (2006.01)
A61B 17/122     (2006.01)
A61B 17/128     (2006.01)
A61B 17/32      (2006.01)
```
(52) U.S. Cl.
CPC .......... *A61B 17/083* (2013.01); *A61B 17/122* (2013.01); *A61B 17/1285* (2013.01); *A61B 17/1227* (2013.01); *A61B 17/320016* (2013.01); *A61B 2017/00323* (2013.01); *A61B 2017/00818* (2013.01); *A61B 2017/00862* (2013.01); *A61B 2017/0409* (2013.01); *A61B 2017/0441* (2013.01); *A61B 2017/0464* (2013.01); *A61B 2017/0496* (2013.01); *A61B 2017/088* (2013.01)

(58) Field of Classification Search
CPC ............ A61B 17/1227; A61B 17/1285; A61B 17/320016; A61B 2017/00818; A61B 2017/0409; A61B 2017/0496
See application file for complete search history.

(56) References Cited

U.S. PATENT DOCUMENTS

| | | | |
|---|---|---|---|
| 5,766,189 | A | 6/1998 | Matsuno |
| 5,921,996 | A | 7/1999 | Sherman |
| 6,551,332 | B1 | 4/2003 | Nguyen et al. |
| 6,814,742 | B2 | 11/2004 | Kimura et al. |
| 7,235,089 | B1 | 6/2007 | McGuckin, Jr. |
| 7,892,244 | B2 | 2/2011 | Monassevitch et al. |
| 7,975,700 | B2 | 7/2011 | Frazier et al. |
| 8,038,612 | B2 | 10/2011 | Paz |
| 8,397,335 | B2 | 3/2013 | Gordin et al. |
| 8,945,155 | B2 | 2/2015 | Gordin et al. |
| 9,463,003 | B2 | 10/2016 | Gordin et al. |
| 10,143,459 | B2 | 12/2018 | Heftman |
| 2005/0251167 | A1 | 11/2005 | Voegele et al. |
| 2013/0253275 | A1* | 9/2013 | Ransden ............ A61B 17/0218 600/204 |
| 2014/0235936 | A1 | 8/2014 | Baas et al. |
| 2016/0000433 | A1 | 1/2016 | Raybin et al. |
| 2017/0181738 | A9* | 6/2017 | Saliman ................ A61F 2/0811 |

FOREIGN PATENT DOCUMENTS

| | | |
|---|---|---|
| JP | 201011973 A | 1/2010 |
| WO | WO 2009/019288 A2 | 2/2009 |
| WO | WO 2013/041960 A1 | 3/2013 |

OTHER PUBLICATIONS

Fujii, T., et al., "A novel endoscopic suturing technique using a specially designed so-called "8-ring" in combination with resolution clips (with videos)", Gastrointestinal Endoscopy 66(6):1215-1220 (2007).

Matsumoto, K., et al., "T1594: A New Traction Device for Gastric Endoscopic Submucosal Dissecton (ESD): Two-Point Fixed by Latex Traction for Early Gastric Cancer", Gastrointestinal Endoscopy, 71(5):AB317 (2010).

Imaeda, H., et al., "Advanced endoscopic submucosal dissection with traction", World Journal of Gastrointestinal Endoscopy 6(7):286-295 (2014).

Sakamoto, N., et al.,"'Loop Clip' a new closure device for large mucosal defects after EMR and ESD", Endoscopy 40:E97-E98 (2008).

Fujihara, S., et al., "Management of a large mucosal defect after duodenal endoscopic resection", World Journal of Gastroenterology, 22(29):6595-6609 (2016).

Mori, H., et al., "The Loop Clip is Useful for Closing Large Mucosal Defects After Colorectal Endoscopic Submucosal Dissection: A Preliminary Clinical Study", Digestive Endoscopy 23:330-331 (2011).

Tsuji, K., et al., "Recent traction methods for endoscopic submucosal dissection", World Journal of Gastroenterology, 22(26):5917-5926 (2016).

Ritsuno, H., et al., "Prospective clinical trial of traction device-assisted endoscopic submucosal dissection of large superficial colorectal tumors using the S-O clip", Surgical Endoscopy 28:3143-3149 (2014).

Sakamoto, N., et al., "The facilitation of a new traction device (S-O clip) assisting endoscopic submucosal dissection for superficial colorectal neoplasms", Endoscopy, 40:E94-E95 (2008).

Takeda, T., et al., "Traction device to remove an adenoma in the appendiceal orifice by endoscopic submucosal dissection", Endoscopy 45:E239-E240 (2013).

Kato, M., et al., "Technical feasibility of line-assisted complete closure technique for large mucosal defects after colorectal endoscopic submucosal dissection", Endoscopy International Open, 5(1):E11-E16 (2017) DOI: http://dx.doi.org/10.1055/s-0042-121002.

* cited by examiner

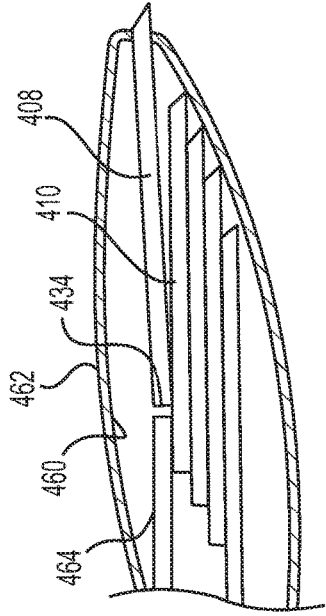
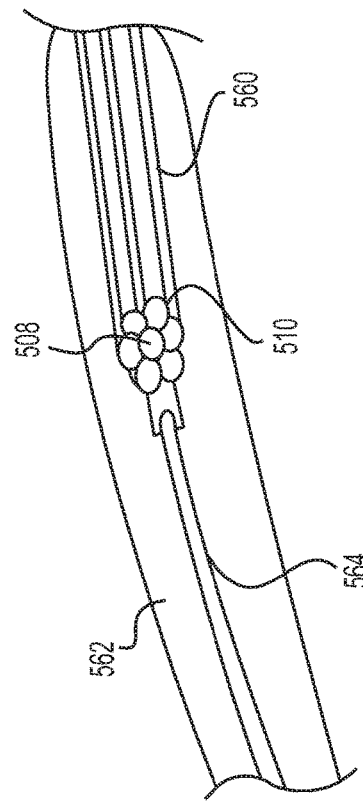
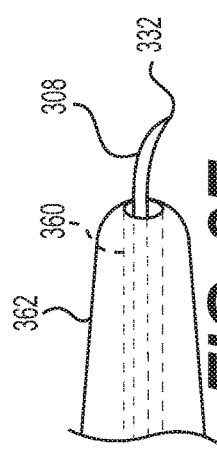
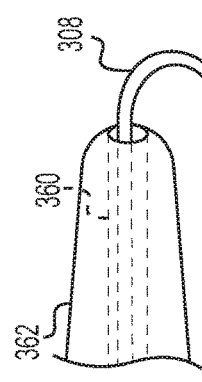
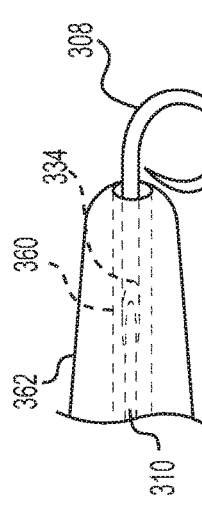
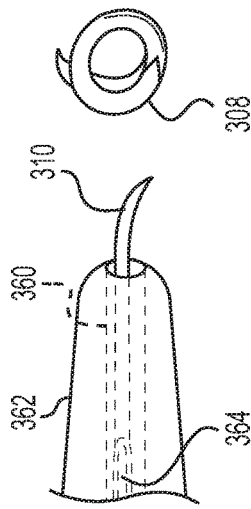

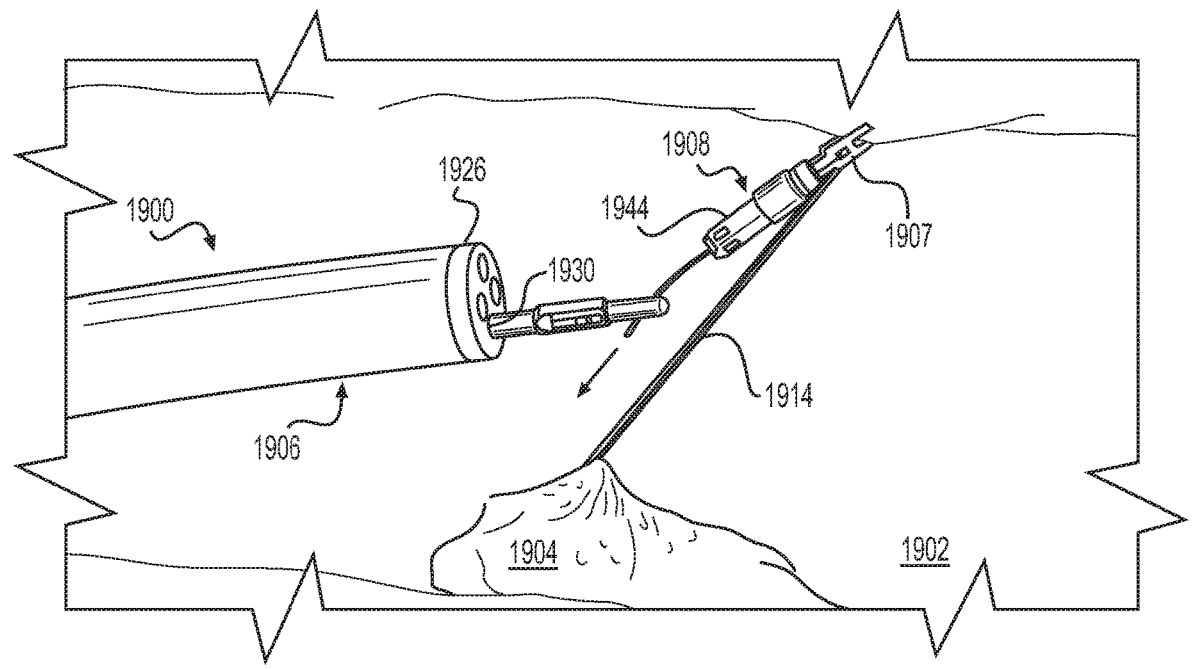
FIG. 19H
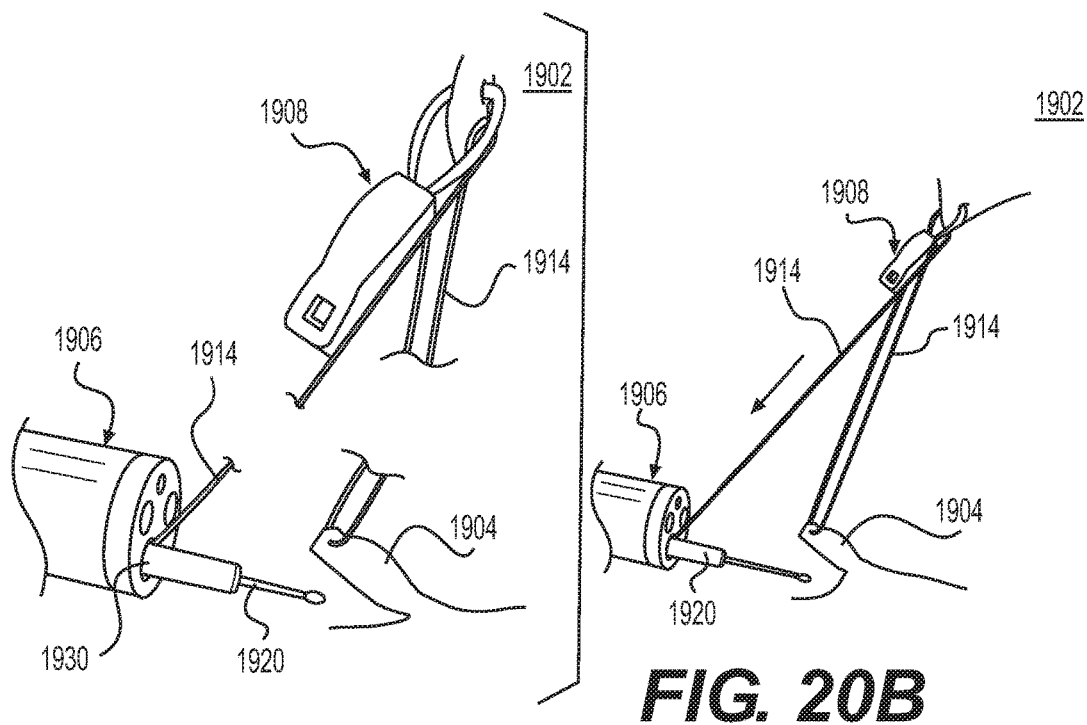
FIG. 20A
FIG. 20B

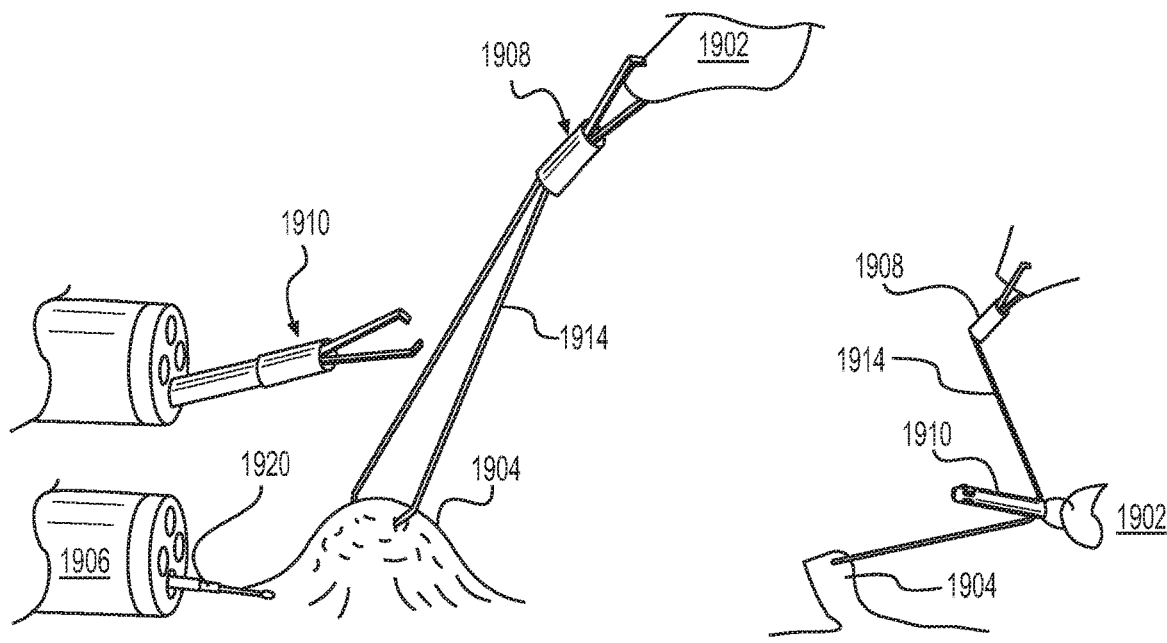
FIG. 21A    FIG. 21B
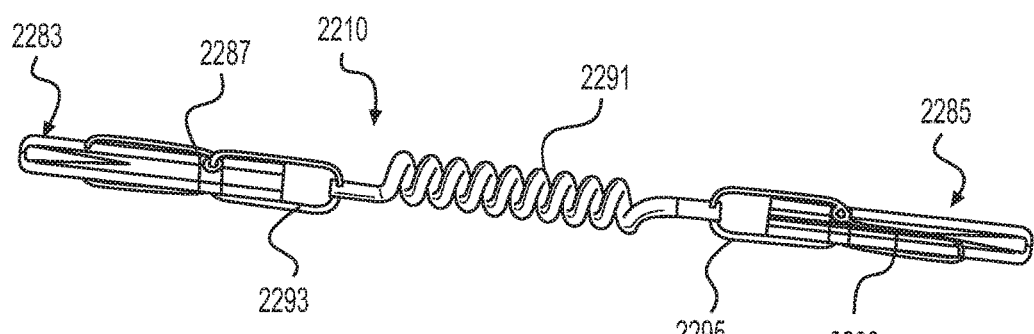
FIG. 22

SYSTEMS, DEVICES, AND RELATED METHODS FOR RETRACTING TISSUE

CROSS-REFERENCE TO RELATED APPLICATIONS

This application claims the benefit of priority from U.S. Provisional Application No. 62/371,471, filed on Aug. 5, 2016, the entirety of which is incorporated by reference herein.

TECHNICAL FIELD

Various aspects of the present disclosure relate generally to tissue retraction. More specifically, the present disclosure relates to systems, devices, and related methods for retracting tissue.

BACKGROUND

Technological developments have given users of medical systems, devices, and methods the ability to conduct increasingly complex procedures on subjects. The removal of tissue in, for example, a subject's gastrointestinal tract, is a type of procedure in which difficulties may arise. One such area of difficulty involves removing a lesion on tissue. In order to remove the lesion, the user may retract tissue at or around the lesion. This retraction may enable the user to clearly observe a cutting plane for removing the lesion. Having this visualization may aid in preventing unwanted incision errors, such as severing vessels. The visualization also may aid in ensuring that as much of or all of the lesion is removed.

In order to achieve retraction, the user may inject a solution into tissue at or around the lesion to elevate the tissue in preparation for cutting. Reaching and elevating the lesion, and in particular, the base of the lesion, may require making a multitude of injections. This may be time consuming. Moreover, the injections may not provide sufficient tissue retraction to provide the line of sight, or other access, desired by the user. These potential problems are exacerbated when the lesion targeted for removal is a flat lesion.

Solutions that offer retraction, while reducing or eliminating the occurrence of the above-described drawbacks, may lead to better outcomes for users and subjects.

SUMMARY

Aspects of the disclosure relate to, among other things, systems, devices, and methods for retracting tissue. Each of the aspects disclosed herein may include one or more of the features described in connection with any of the other disclosed aspects.

In one aspect of the present disclosure, a tissue retraction system may include a first anchor, a second anchor, and an elongate coupling member extending between the first anchor and the second anchor. The system also may include a holder for receiving the first anchor, the second anchor, and the elongate coupling element. The holder may include a proximal portion and a distal portion. The distal portion may have a smaller width than the proximal portion such that the distal portion exerts a force on a proximal end of the first anchor during deployment of the first anchor from the holder. The force may move the first anchor into an open configuration for receiving tissue.

Aspects of the tissue retractions system may include one or more of the features below. The first anchor may abut the second anchor in the holder. The first anchor may include a first jaw and a second jaw, and the first jaw may be pivotably attached to the second jaw. The first anchor may further include a biasing element that biases at least one of the first jaw and the second jaw to move toward the other of the first jaw and the second jaw. The second anchor may include a third jaw and a fourth jaw, and the third jaw may be pivotably attached to the fourth jaw. Distal ends of the third jaw and the fourth jaw may engage opposing surfaces of proximal ends of the first jaw and the second jaw in the holder.

In another aspect of the present disclosure, a redeployable clip system for tissue may include a clip. The clip may include a fastening element having a first configuration for receiving tissue, and a second configuration for engaging tissue. The clip also may include a base for receiving at least a portion of the fastening element. The fastening element may move to the first configuration when moved away from the base, and the fastening element may move to the second configuration when moving toward the base. The clip also may include an actuation element at least partially received within the base for moving the fastening element between the first configuration and the second configuration. The actuation element may include an engagement element. The system also may include an instrument. The instrument may include a manipulation element for engaging the engagement element. The instrument also may include a receiver for receiving at least a portion of the base to fix the base relative to the receiver. The manipulation element may be configured to position the base for fixing relative to the receiver. Moving the actuation element relative to the base when the base is fixed on the receiver may move the fastening element between the first configuration and the second configuration.

Aspects of the redeployable clip system may include one or more of the features below. The receiver may include a first coupling element. The base may include a second coupling element. The first coupling element may releasably couple to the second coupling element to fix the base relative to the receiver. The first coupling element may include one of a groove and a protrusion configured for receipt in the groove. The second coupling element may include the other of the groove and the protrusion. The first coupling element may include internal geometric features. The second coupling element may include external geometric features that mate with the internal geometric features. The first coupling element and the second coupling element may form a snap-fit connection. The manipulation element may include an arm having a bent distal end and the engagement element may include a loop. The manipulation element may include a ball and the engagement element may include a socket. The ball may be releasably coupled to the socket.

In yet another aspect of the present disclosure, a method for retracting tissue may include anchoring a first element to tissue at a first location. The method also may include anchoring a second element to tissue at a second location. The second location may be spaced from the first location. The anchoring of the second element to the tissue may cause tension to build in a portion of a coupling element that extends between the first element and the second element, such that the first element, the coupling element, and the second element may exert a force on the tissue at the first location. The force may have a direction of application and a magnitude. The method also may include manipulating the tissue at the first location while the force is exerted on the tissue at the first location.

Aspects of the method for retracting tissue may include one or more of the features below. Releasing the second element from the tissue at the second location. Moving the second element toward tissue at a third location, the third location being spaced from the second location. Anchoring the second element to the tissue at the third location. Adjusting the magnitude of the force by drawing the first element toward the second element using the coupling element. Ejecting the first element from a holder. Engaging the first element with the holder to move the first element to an open configuration to receive the tissue at the first location. Disengaging the first element from the holder to move the first element to a closed configuration to anchor the first element to the tissue at the first location.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIGS. 3F-3I show a holder and anchors of the retraction system of FIGS. 3A-3E, in accordance with aspects of the present disclosure.

FIG. 4 shows a cutaway view of an assembly including a holder, anchors, and a pusher, in accordance with aspects of the present disclosure.

FIG. 5 shows a cutaway view of another assembly including a holder, anchors, and a pusher, in accordance with aspects of the present disclosure.

FIGS. 19A-19H show another retraction system in use, in accordance with aspects of the present disclosure.

FIGS. 20A and 20B show another version of the retraction system of FIGS. 19A-19H in use, in accordance with aspects of the present disclosure.

FIGS. 21A and 21B show another version of the retraction system of FIGS. 19A-19H in use, in accordance with aspects of the present disclosure.

FIG. 22 shows an auxiliary anchor, in accordance with aspects of the present disclosure.

DETAILED DESCRIPTION

The present disclosure is drawn to systems, devices, and methods for retracting tissue. Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. The term "retraction" may refer, for example, to positioning tissue to expose and/or visualize a cutting plane for removing the tissue. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

Figure 1A:
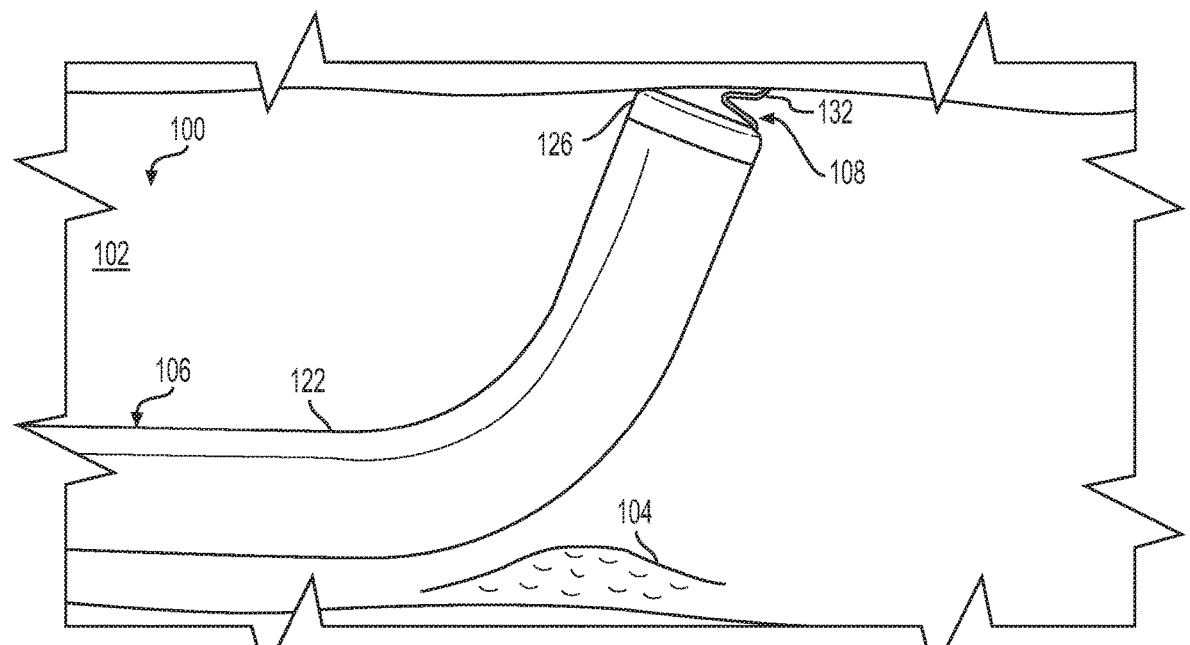
FIGS. 1A-1H show a retraction system in use, in accordance with aspects of the present disclosure.
Figure 1B:
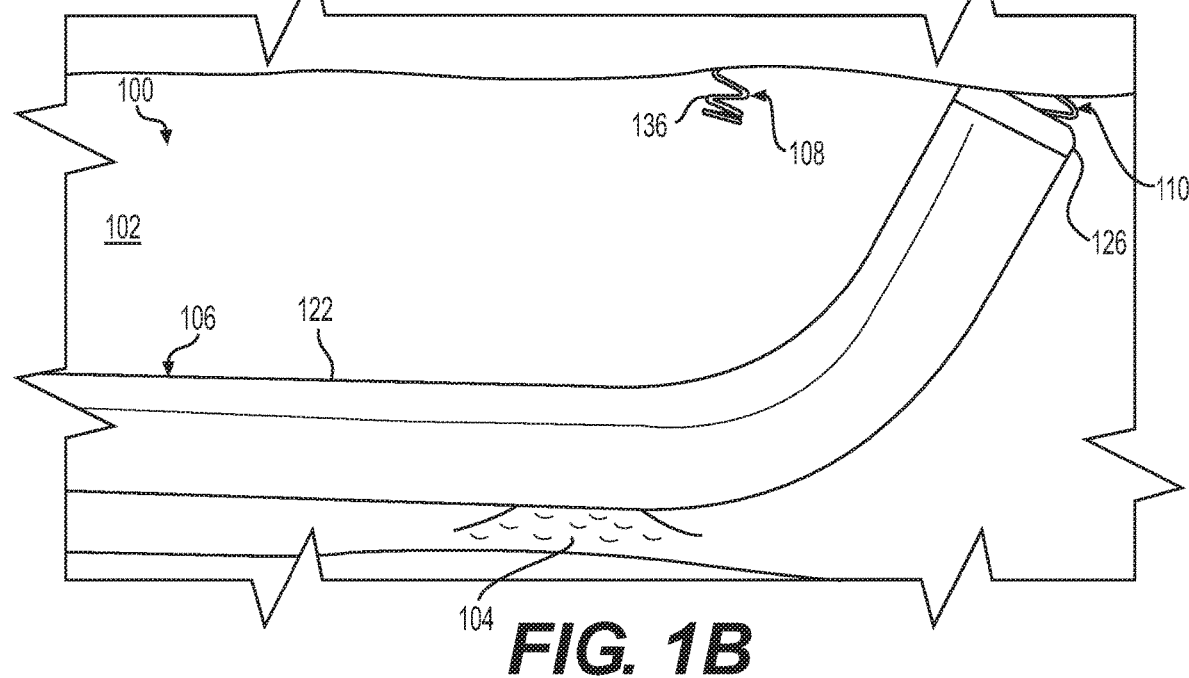

FIGS. 1A-1H show a system 100 for retracting a portion of tissue 102. Tissue 102 may include, for example, an area 104 targeted for removal, such as an area with a lesion. System 100 may include an introducer 106 for providing access to tissue 102. Introducer 106 may deploy anchors 108 and 110 into portions of tissue 102 opposing, or otherwise facing, target area 104. Additionally or alternatively, introducer may deploy anchors 108 and 110 into portions of tissue spaced apart from target area 104. FIGS. 1A and 1B show anchors 108 and 110 being deployed.

Figure 1C:
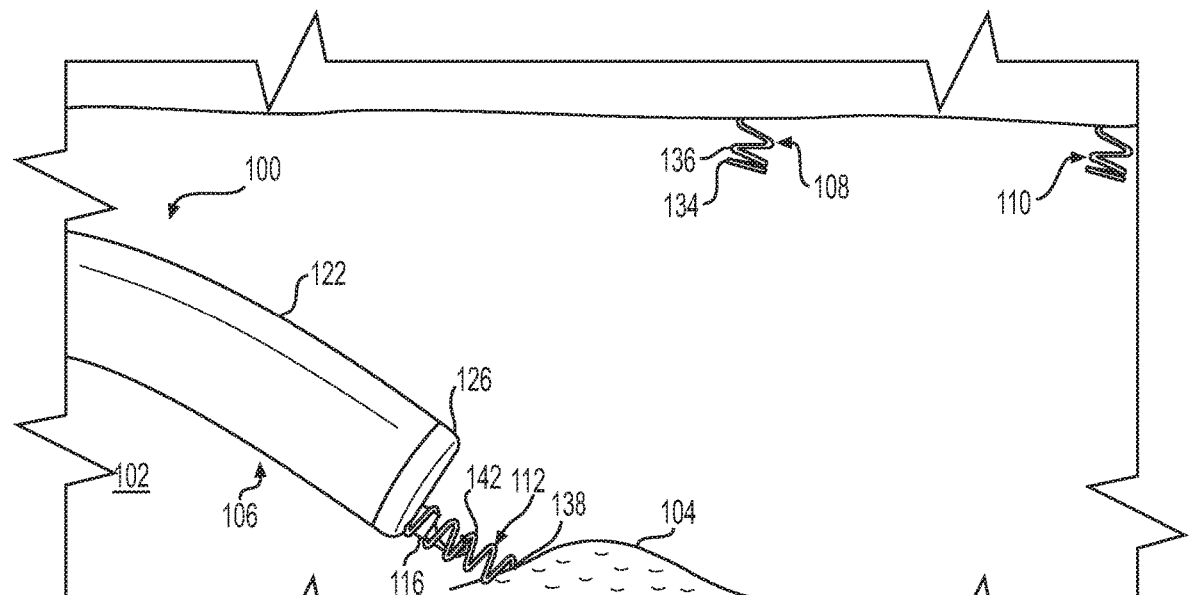
Figure 1D:
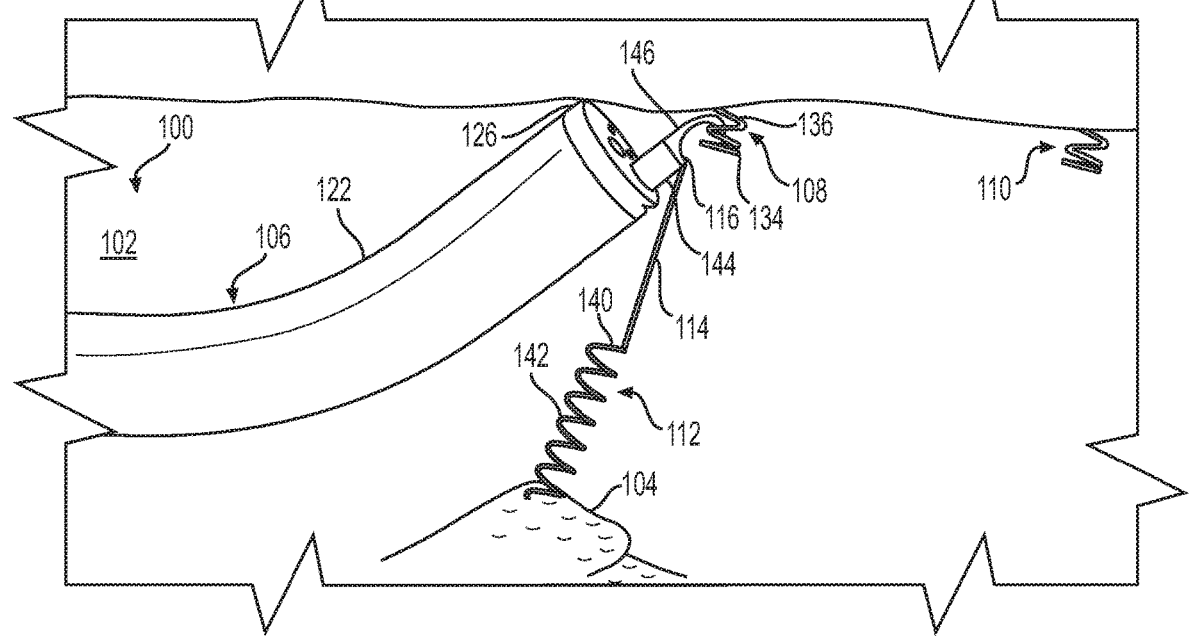

Introducer 106 also may deploy an anchor 112 into target area 104, as shown in FIG. 1C. A tether 114, visible in FIG. 1D, may be coupled to anchor 112. A clip 116 may be coupled to tether 114. Introducer 106 and a positioning instrument (not visible in FIG. 1D) therein may attach clip 116 to anchor 108 to retract target area 104. A cutting instrument 120, shown in FIG. 1E, may be used to cut the retracted target area 104.

Figure 1E:
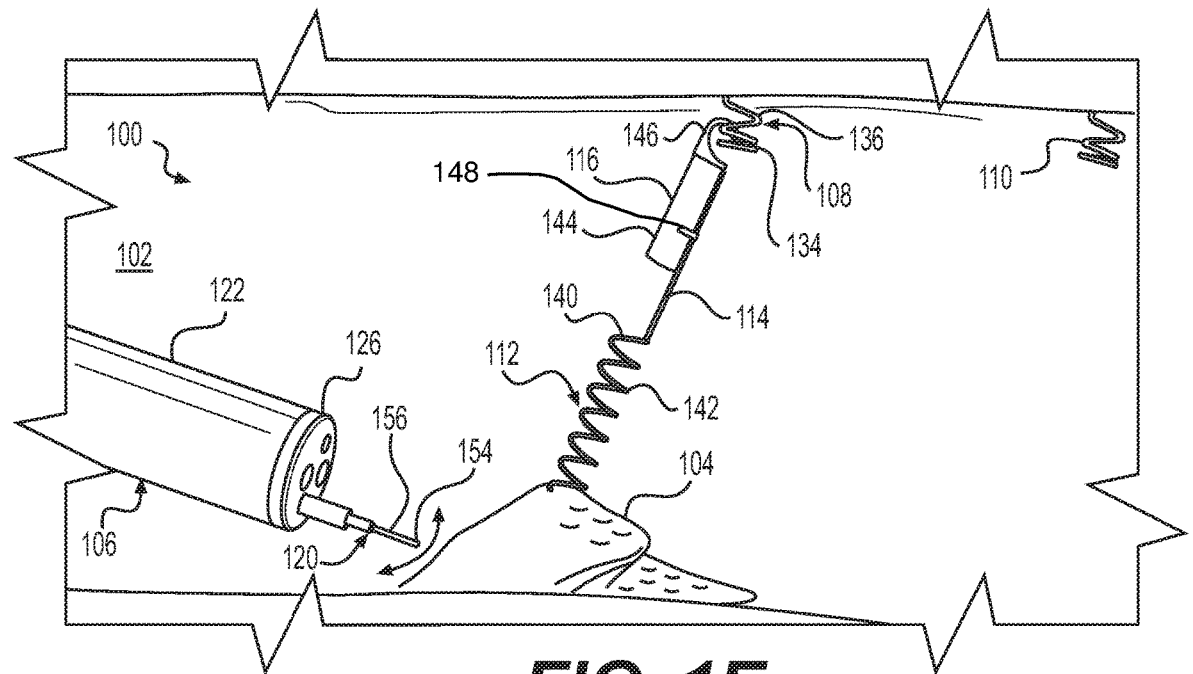
Figure 1F:
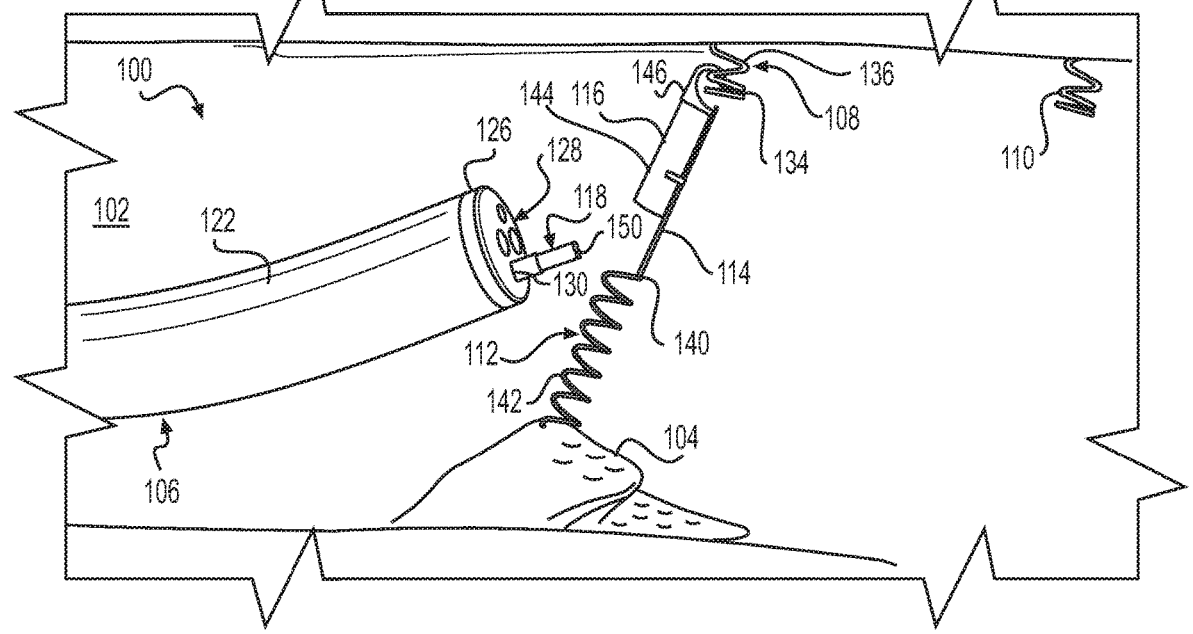
Figure 1G:
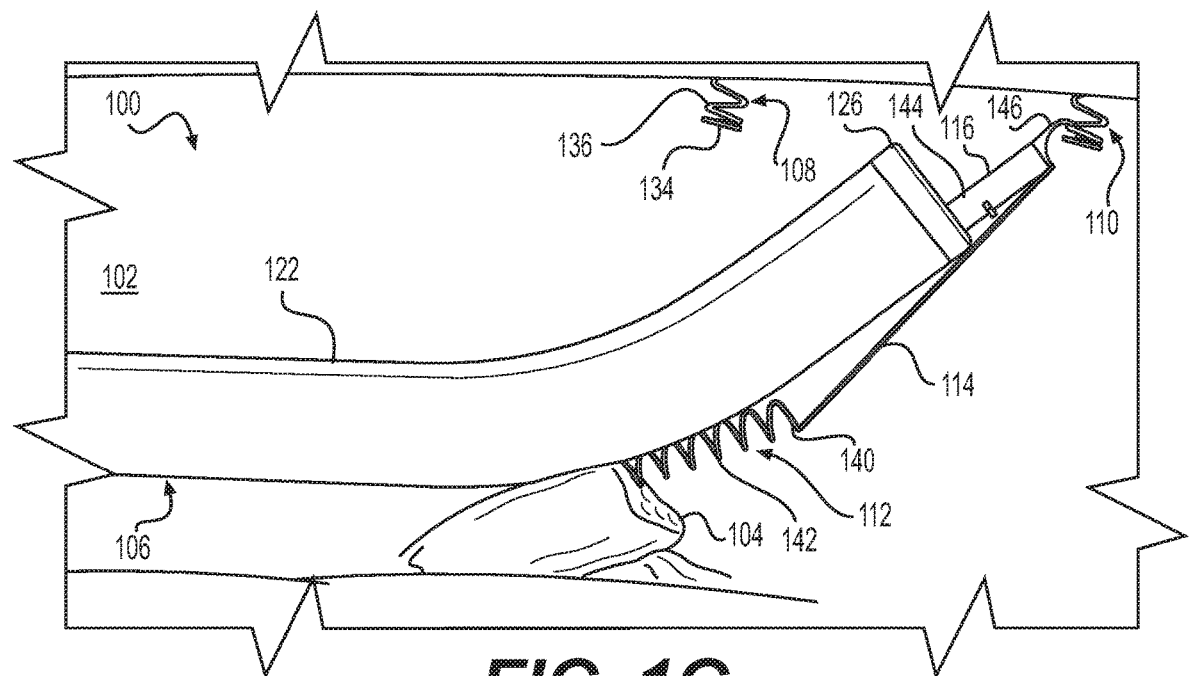
Figure 1H:
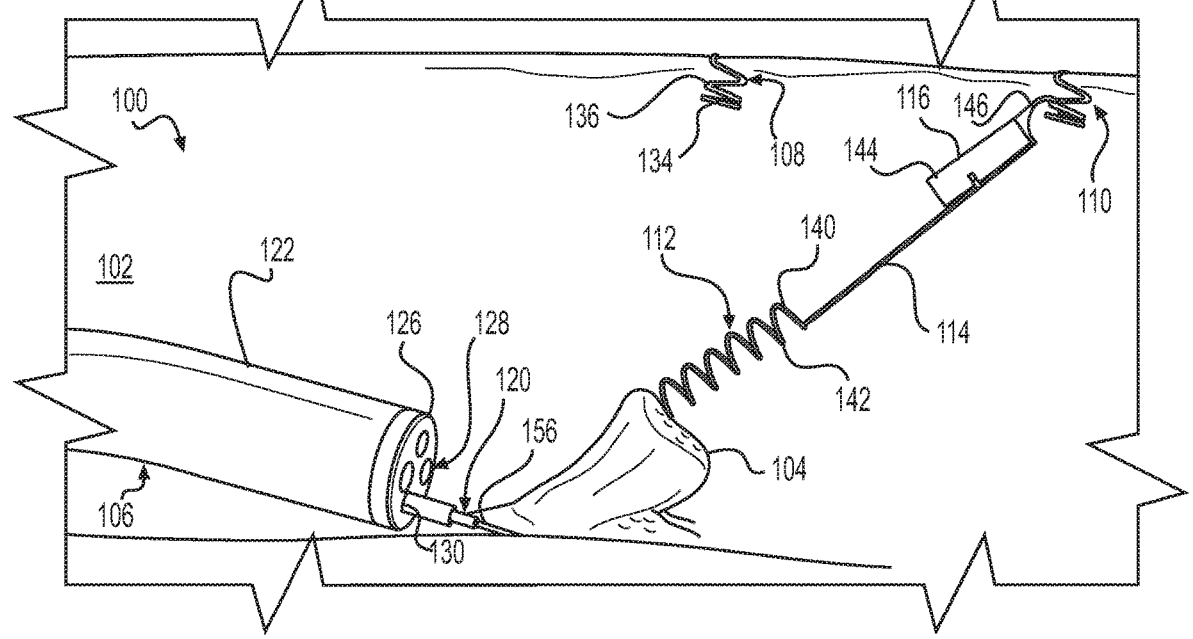

FIGS. 1F and 1G show introducer 106 and positioning instrument 118 removing clip 116 from anchor 108, and attaching clip 116 to anchor 110, to further retract target area 104. Anchors 108 and 110 may act as staged pull points for retracting target area 104. The space between anchors 108 and 110 may provide a user with the ability to implement different vectors of retraction (e.g., directions and/or magnitudes of retraction) for retracting target area 104. This control over the vector of retraction may provide the user with an enhanced ability to expose and/or visualize the cutting plane the user will use to guide cutting of target area 104 with cutting instrument 120. FIG. 1H shows cutting instrument 120 cutting the retracted target area 104 after adjustment of the retraction vector.

Introducer 106 may include an elongate tubular member 122. Elongate tubular member 122 may include lumens (not shown) that extend lengthwise through the interior of elongate tubular member 122. The lumens may receive one or more of an instrument, a lighting element (not shown), an imaging element (not shown), and/or a flow of fluid or other material (not shown) entering into or exiting from target area 104.

An end cap 126 may cover the distal end of elongate tubular member 122. End cap 126 may include ports 128 that communicate with the lumens (see, for example, FIGS. 1F and 1H). A port 130 may communicate with the instrument lumen. An instrument inserted through the instrument lumen may extend out of the distal end of introducer 106 via port 130. The other ports 128 may communicate with the other lumens to receive the lighting element, imaging element, and/or flow of fluid or other material. A user of introducer 106 may use the lighting element and the imaging element to visualize target area 104 and its surroundings. Introducer 106 may include, for example, any suitable type of endoscope, sheath, or catheter.

Introducer 106 also may include a handle (not shown) having a steering mechanism (not shown) mounted thereon. The steering mechanism may be coupled to one or more steering wires or cables that may extend lengthwise through elongate tubular member 122. By manipulating the steering mechanism to exert tension and/or compression forces on the steering wires or cables, the user may control deflection of the distal end of introducer 106.

Anchor 108 may include a first end 132 (abutting tissue 102 in FIG. 1A) configured to penetrate into tissue 102. First end 132 may include, for example, a sharp penetrating tip. Anchor 108 also may include a second end 134 (visible in FIGS. 1B-1H) opposite first end 132. Second end 134 may serve as an attachment point. For example, second end 134 may include a loop, eyelet, hook, or any other suitable attachment element.

The intermediate portion of anchor 108 between first end 132 and second end 134 may move between a contracted or rest configuration and an extended or stretched configuration. When stretched, anchor 108 may exert a biasing force that tends to bring first end 132 and second end 134 toward each other. For example, the intermediate portion of anchor 108 may include a helical tension spring 136.

Helical tension spring 136 also may offer functionality in addition to providing the biasing force. For example, rotating helical tension spring 136 in one of a clockwise direction and a counterclockwise direction may facilitate penetration of first end 132 deeper into tissue 102, similar to operation of a corkscrew. Rotating helical tension spring 136 in the other of the clockwise direction and the counterclockwise direction may facilitate moving first end 132 back out of tissue 102. This may provide the user with the ability to control the depth of penetration of anchor 108 into tissue 102.

Anchor 110 may include one or more of the features of anchor 108. In one example, anchor 110 may be identical to anchor 108. Anchor 110, however, may be deployed into tissue 102 at a position spaced apart from anchor 108. As will be explained in detail below, due to the spacing of anchors 108 and 110, anchors 108 and 110 may act as staged pull points that impart different vectors of retraction onto target area 104.

Anchor 112 also may include or more of the features of anchor 108. For example, anchor 112 may include a first end 138 configured to penetrate tissue at target area 104 (as seen in FIG. 1C), a second end 140 opposite first end 138, and a helical tension spring 142 connecting first end 138 to second end 140 (a seen in FIGS. 1D-1H). In one example, a length of anchor 112 may be greater than a length of anchor 110. The depth of penetration of anchor 112 in target area 104 may be controlled by rotating anchor 112 in either of the clockwise and counterclockwise directions.

Tether 114 may include a wire, a cord, a cable, an elastic band (e.g., a rubber band), a spring (e.g., a helical tension spring), a suture, a high carbon spring wire, a braided or wound filament, stainless steel, nitinol, spring steel, music wire, muscle wire, and/or any other suitable elongate member. Tether 114 may be metallic, polymeric, or a combination of metallic and polymeric. One end of tether 114 may be attached to second end 140 of anchor 112 (as seen in FIGS. 1D-1H). The other end of tether 114 may be attached to clip 116. Clip 116 may include a base element 144. One end of base element 144 may be attached to an engagement element 146. Engagement element 146 may be configured to releasably couple to the second ends of anchors 108 and 110. Tether 114 may attach to clip 116 where base element 144 meets engagement element 146. Alternatively, tether 114 may attach to clip 116 at any other suitable location on clip 116.

An outer surface of base element 144 may include a shoulder or abutment 148 thereon. Shoulder 148 may include one or more protrusions protruding from the outer surface. Shoulder 148 may engage anchor 112, as described below. In an example where tether 114 includes a helical tension spring, tether 114 may be integral with helical tension spring 142 of anchor 112.

An end of base element 144, opposite the end attached to engagement element 146, may include an opening (not shown). The opening may receive a tip portion 150 of a positioning instrument 118, permitting receipt of tip portion 150 within base element 144 such that clip 116 may move with tip portion 150. FIG. 1F shows tip portion 150 prior to its insertion into base element 144, and FIG. 1G shows tip portion 150 within base element 144 (with tip portion 150 being obscured by base element 144). A shaft portion (not shown) of positioning instrument 118 may extend proximally through the instrument lumen. The user may manipulate the shaft portion to extend and retract tip portion 150 out of and into introducer 106, respectively, and/or to otherwise move tip portion 150. The shaft portion may be flexible enough to deflect with introducer 106 when introducer 106 is deflected by the user.

Prior to being deployed, positioning instrument 118, anchors 108, 110, and 112, and tether 114 may be housed within the instrument lumen. This may, for example, prevent anchors 108, 110, and 112 from prematurely engaging tissue as the distal end of introducer 106 navigates towards target area 104. In the instrument lumen, tip portion 150 of positioning instrument 118 may be received within base element 144 of clip 116. Anchor 112 may surround clip 116. Second end 140 of anchor 112 may engage shoulder 148.

First end 138 of anchor 112 may engage the second end of anchor 110. The first end of anchor 110 may engage second end 134 of anchor 108. First end 132 of anchor 108 may be recessed from port 130.

Once the distal end of introducer 106 is positioned relative to target area 104, the user may deflect the distal end of introducer 106 in preparation for deploying anchor 108 into tissue 102. Deploying anchor 108 may include moving positioning instrument 118 distally to extend at least first end 132 of anchor 108 out of port 130 and into contact with tissue 102 (FIG. 1A). Deploying anchor 108 also may include rotating positioning instrument 118 about its central longitudinal axis. This rotation may rotate clip 116, anchor 112, anchor 110, and anchor 108, through the chain of engagement between these elements. As first end 132 of anchor 108 rotates, first end 132 may penetrate into tissue 102, and may burrow deeper into tissue 102 with continued rotation. When the desired depth of penetration is reached, positioning instrument 118 and introducer 106 may be moved away from anchor 108, leaving anchor 108 in place in tissue 102. Anchor 110 may be deployed into tissue 102 in a similar manner at another position (see FIG. 1B). Anchor 112 also may be deployed into target area 104 in a similar manner (see FIG. 1C).

Positioning instrument 118, and clip 116 mounted thereon, may move further and further distally during deployment and release of anchors 108, 110, and 112. By the time anchor 112 is being deployed, engagement element 146 may extend distally out of the instrument lumen and port 130, as shown in FIG. 1C. With first end 138 of anchor 112 embedded in target area 104, the user may move introducer 106, positioning instrument 118, and clip 116 (whose base element 144 may still be mounted on tip portion 150 of positioning instrument 118) toward anchor 108. This movement may impart a tensile force on tether 114, which may pull anchor 112 and target area 104. The retraction may be along a vector extending between target area 104 and anchor 108. The movement also may stretch anchors 108 and 112, and/or tether 114.

With anchors 108, 110, and 112; tether 114; and clip 116 deployed, positioning instrument 118 may be withdrawn from the instrument lumen to allow insertion of cutting instrument 120. Cutting instrument 120 may be guided distally through the instrument lumen, and extended distally out of port 130 to the position shown in FIG. 1E. Cutting instrument 120 may include a distal cutting element 154. Cutting element 154 may include, for example, a blade, an electrosurgical electrode, a heating element, and/or any other element suitable for cutting tissue 102. A shaft 156 may extend proximally from cutting element 154, through the instrument lumen, and to the proximal end of introducer 106. Shaft 156 may be operatively coupled to a power source, such as an electrosurgical unit or other suitable power source, to provide the energy for cutting tissue 102. Alternatively, positioning instrument 118 may be left in place, and cutting instrument 120 may be introduced through another lumen.

The user may remove target area 104 by sweeping the distal end of introducer 106 back-and-forth, thereby sweeping cutting element 154 back-and-forth across the retracted target area 104 (as indicated by the two-headed arrow near cutting element 154 in FIG. 1E). Other movements of cutting element 154, including stabbing, twisting, lifting, lowering, and the like, may also be performed. As cutting element 154 cuts target area 104, target area 104 may form a flap that may be drawn toward anchor 108 by tension and/or biasing forces in anchor 112, tether 114, and/or anchor 108. This may lead to a reduction in the retraction force exerted on target area 104. In order to increase the retraction force, the user may withdraw cutting instrument 120 from the instrument lumen. The user may reintroduce positioning instrument 118 into the instrument lumen, and navigate positioning instrument 118 until tip portion 150 once again extends distally out of port 130, as depicted in FIG. 1F. Tip portion 150 may re-enter base element 144 of clip 116. Tip portion 150, with the assistance of introducer 106, may move clip 116 to release engagement element 146 from second end 134 of anchor 108. Tip portion 150 and introducer 106 then may move clip 116 to bring engagement element 146 into engagement with the second end of anchor 110, as seen in FIG. 1G. This movement may impart a tensile force on tether 114, which may pull anchor 112, and thereby further retract target area 104. The retraction may be along a vector extending between target area 104 and anchor 110. The movement of clip 116 to anchor 110 also may stretch anchors 110, 112, and/or tether 114.

Positioning instrument 118 may once again be withdrawn from the instrument lumen to make room for cutting instrument 120. The user may continue cutting the retracted target area 104 using cutting instrument 120, as shown in FIG. 1H. Alternatively, positioning instrument 118 and cutting instrument 120 may be positioned in different lumens of introducer 106, and one need not be withdrawn to make way for the other. It should be understood that additional anchors may have been deployed into tissue 102 along with anchors 108 and 110, allowing the user to further retract target area 104 to assist with cutting. The process steps described above may be repeated until target area 104 is removed.

Figure 2:
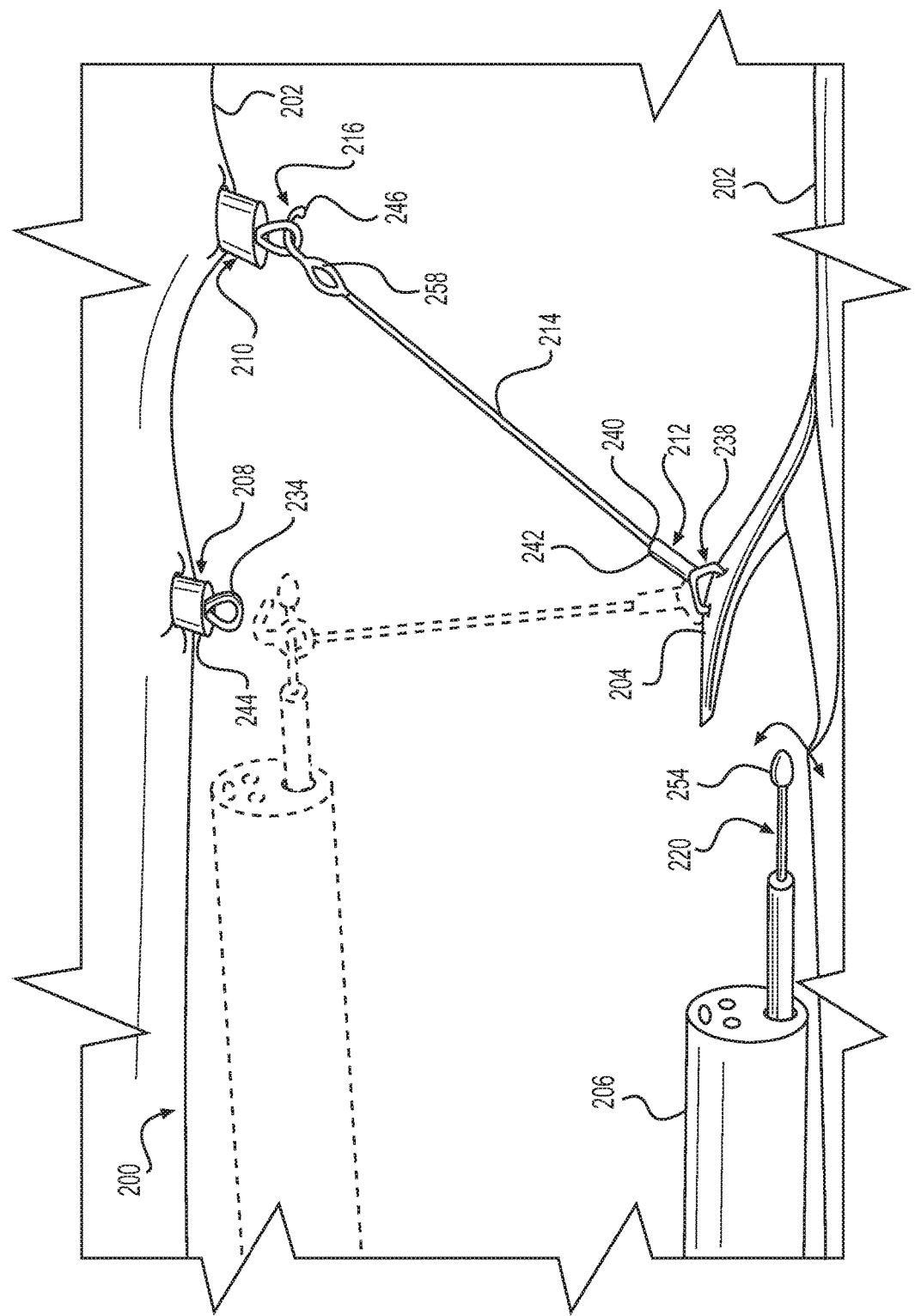
FIG. 2 shows another retraction system in use, in accordance with aspects of the present disclosure.

FIG. 2 shows another system 200 for retracting tissue 202 at a target area or lesion 204. Like system 100, system 200 may include an introducer 206, a cutting instrument 220, anchors 208 and 210 for embedding into tissue 202 to act as staged pull points, an anchor 212 for embedding in target area 204, a tether 214 for linking anchor 212 to anchors 208 and 210, and a clip 216 at an end of tether 214 for engaging anchors 208 and 210.

System 200 may differ from system 100 in a variety of ways. For example, anchor 208 may include a base element 244 having a fastener (not shown) attached to a first end. The fastener may be embedded into tissue 202 to secure anchor 208 to tissue 202. The fastener may include, for example, a helical penetrating end similar to anchor 108. An engagement element 234 may be attached to a second end of base element 244. Engagement element 234 may include a loop or eyelet. Anchor 210 may be similar to, or even identical to, anchor 208.

Anchor 212 may include a base element 242 having a fastener 238 at a first end, and tether 214 at a second end 240. Fastener 238 may include, for example, a grasping element formed by jaws. It is contemplated that the jaws may move between an open position for receiving tissue and a closed position for grasping the received tissue. The fasteners of anchors 208 and 210 also may be similar to fastener 238. Any suitable positioning instrument (not shown) may be configured to actuate the jaws between the open position and the closed position. Exemplary positioning instruments are described below. Alternatively, a positioning instrument similar to positioning instrument 118 of system 100 may be used to deploy anchors 208, 210, and 212; tether 214; and clip 216 from introducer 206.

A first end of tether 214 may be attached to second end 240 of anchor 212. A second end of tether 214 may be attached to clip 216. Clip 216 may include an engagement element 246 configured for receipt in engagement element 234 of anchor 208 (and the engagement element of anchor 210) to attach clip 216 to anchor 208. Clip 216 also may include an aperture or eyelet 258 configured to receive cutting instrument 220.

Any suitable positioning instrument may be used to deploy anchors 208, 210, and 212; tether 214; and clip 216 from within an instrument lumen of introducer 206. With anchors 208, 210, and 212; tether 214; and clip 216 deployed, and the positioning instrument withdrawn from the instrument lumen, cutting instrument 120 may be guided distally through the instrument lumen and extended distally out of introducer 206. Alternatively, the positioning instrument and cutting instrument 120 may occupy different lumens of introducer 206, and one need not be removed to make way for the other.

The user may insert the distal end of cutting instrument 220 into aperture 258 of clip 216. Using movement of introducer 206 and cutting instrument 220, the user may pull clip 216 toward anchor 208 (shown in dashed line in FIG. 2). The user may attach engagement element 246 of clip 216 to engagement element 234 of anchor 208. These movements may impart a tensile force on tether 214, which may pull anchor 212, and thereby retract target area 204. The retraction may be along a vector extending between target area 204 and anchor 208. The movement also may stretch tether 214.

With target area 204 retracted, the user may sweep a cutting element 254 of cutting instrument 220 across the retracted target area 204. As cutting element 254 cuts target area 204, target area 204 may form a flap that may be drawn toward anchor 208 by tension and/or biasing forces in tether 114. This may lead to a reduction in the retraction force on target area 204. In order to increase the retraction force, the user may reinsert cutting instrument 220 into aperture 258 of clip 216. The user may move clip 216, using cutting instrument 220 and introducer 206, to release engagement element 246 from engagement element 234 of anchor 108. Cutting instrument 220 then may move clip 216 to bring engagement element 246 into engagement with the engagement element of anchor 210 (shown in solid line in FIG. 2). This movement may impart a tensile force on tether 214, which may pull anchor 212, and thereby further retract target area 204. The retraction may be along a vector extending between target area 204 and anchor 210. The movement also may stretch tether 214.

The user may cut the further-retracted target area 204 using cutting instrument 220. It should be understood that additional anchors may have been deployed into tissue 202 along with anchors 208 and 210, allowing the user to further retract target area 204 to assist with cutting, by executing the above-described steps. The process may be repeated until target area 204 is removed.

It should be understood that aspects of system 200 may be used interchangeably with aspects of system 100. For example, one or more of anchors 208, 210, and 212; tether 214; and clip 216 of system 200 may be used in place of anchors 108, 110, and 112; tether 114; and clip 116 of system 100. The opposite also is contemplated. That is, one or more of anchors 108, 110, and 112; tether 114; and clip 116 of system 100 may be used in place of anchors 208, 210, and 212; tether 213; and clip 216 of system 200.

FIGS. 3A-3I show another system 300 for retracting tissue. FIGS. 3A-3E show system 300 in use in a subject. FIGS. 3F-3I show a portion of system 300 being used, to more clearly show certain aspects of system 300. System 300 may include an introducer 306 (similar to introducer 106) for deploying anchors 308 and 310 into tissue 302 to act as staged pull points. Prior to deployment, anchors 308 and 310 may be received in a lumen 360 of a holder 362 (the lumen being shown in FIGS. 3F-3I). Holder 362 may be slidable within an instrument lumen (not shown) of introducer 306, such that the user may retract holder 362 into the instrument lumen during navigation of introducer 306 to a target area, and extend holder 362 out of the distal end of introducer 306 to facilitate deployment of anchors 308 and 310 into tissue 302. While within lumen 360, anchors 308 and 310 may be constrained by the surfaces of holder 362 that form lumen 360 (see FIGS. 3F-3I). For example, anchors 308 and 310 may be held in a straightened configuration by the interior surfaces of holder 362.

Anchors 308 and 310 may be serially arranged in lumen 360. A first end 332 of anchor 308 may extend toward the distal end of holder 362. A second end 334 of anchor 308 may engage a first end of anchor 310, as seen in FIG. 3H. In one example, anchor 308 may be integral with anchor 310, with anchors 308 and 310 being connected by a frangible portion. Alternatively, anchors 308 and 310 may be discrete segments, with second end 334 of anchor 308 abutting the first end of anchor 310.

Figure 3A:
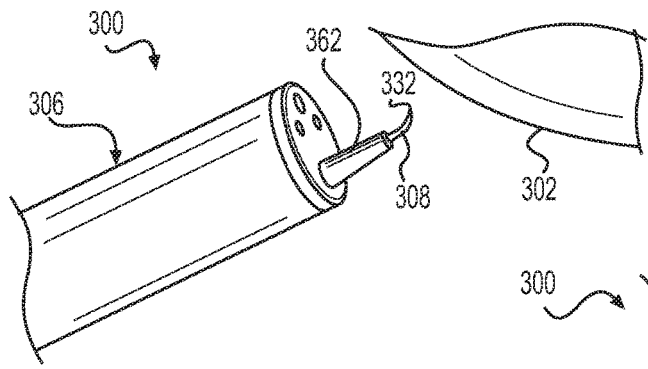
FIGS. 3A-3E show yet another retraction system in use, in accordance with aspects of the present disclosure.
Figure 3B:
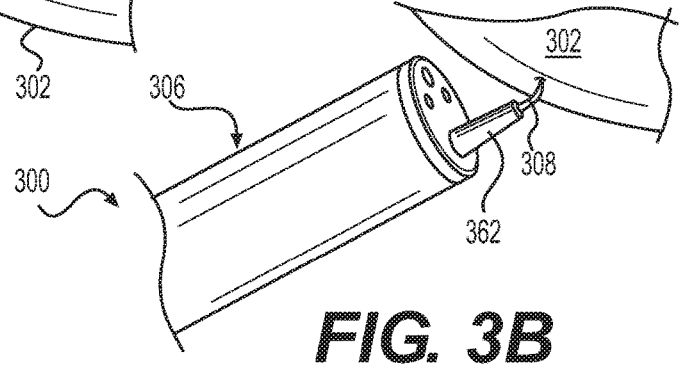
Figure 3C:
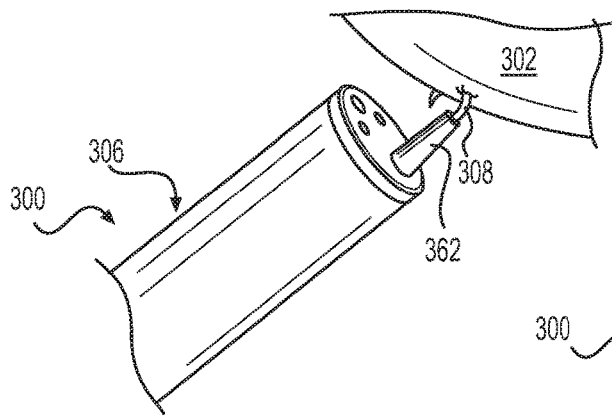
Figure 3D:
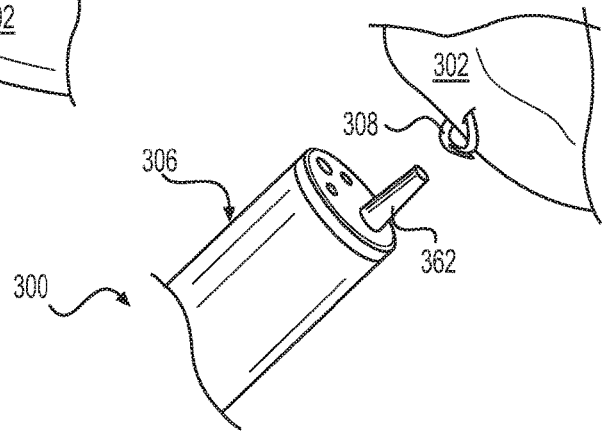
Figure 3E:
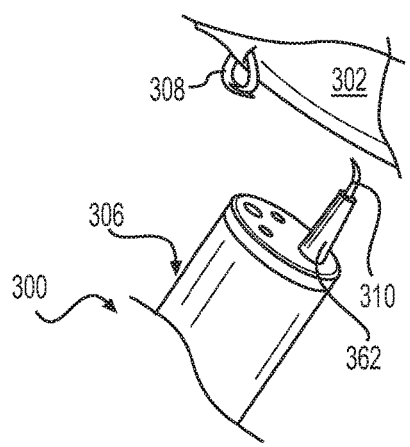

The second end of anchor 310 may engage a distal end of a pusher or plunger 364. The user may move pusher 364 distally to push anchors 308 and 310 distally through lumen 360. With continued distal movement, pusher 364 may cause first end 332 of anchor 308 to extend out of holder 362. First end 332 may penetrate tissue 302 (see FIGS. 3A, 3B, and 3F). As more of anchor 308 extends out of holder, the exposed portion of anchor 308 may begin returning to its unconstrained configuration (see FIGS. 3C, 3G, and 3H). The unconstrained configuration may include, for example, the loop configuration shown in FIGS. 3D, 3E, and 3I, or alternatively, a triangle, a hook, a staple, or any other suitable shape. Anchor 308 may be made of any suitable material, including wire, stainless steel, nitinol, high carbon spring steel, a polymeric material that includes shape memory, and/or bio-absorbable materials. Once anchor 308 is freed from holder 362, it may separate from anchor 310 and remain on tissue 302 (see FIGS. 3D and 3I). The first end of anchor 310 may extend out of holder 362, and the deployment process may repeat for deploying anchor 310 at a location spaced apart from anchor 308 (FIGS. 3E and 3I). While two anchors 308 and 310 are depicted, it should be understood that any number of anchors may be received in holder 362 depending on how many staged pulling points the user wants to set.

FIG. 4 shows another holder 462. Holder 462 may be similar to holder 362 of system 300, except anchors 408 and 410, along with any additional anchors, may be stacked. Anchors 408 and 410 may partially overlap, instead of being arranged end-to-end end like anchors 308 and 310. A lumen 460 of holder 462 may be wider than lumen 360 of holder 362 to accommodate the stacked anchors 408 and 410. A plunger or pusher 464, similar to plunger or pusher 364 of system 300, may push a proximal end 434 of anchor 408 distally to deploy anchor 408 into tissue. Plunger 464 may then retract and move to engage a proximal end of anchor 410 in preparation for deploying anchor 410. This process may be repeated to deploy all of the anchors in holder 462.

FIG. 5 shows a holder 562. Holder 562 may be similar to holders 362 and 462 of systems 300 and 400, respectively. In holder 562, anchors 508 and 510, along with any other anchors, may be arranged side-by-side in a bundle formation within a lumen or chamber 560. A plunger or pusher 564, similar to plunger or pushers 364 and 464 of systems 300 and 400, respectively, may push proximal ends of the anchors distally, one at a time, to deploy the anchors into tissue. Between deployments, plunger 564 may be retracted and positioned at a proximal end of the next anchor in preparation for deployment of the next anchor.

Figure 6:
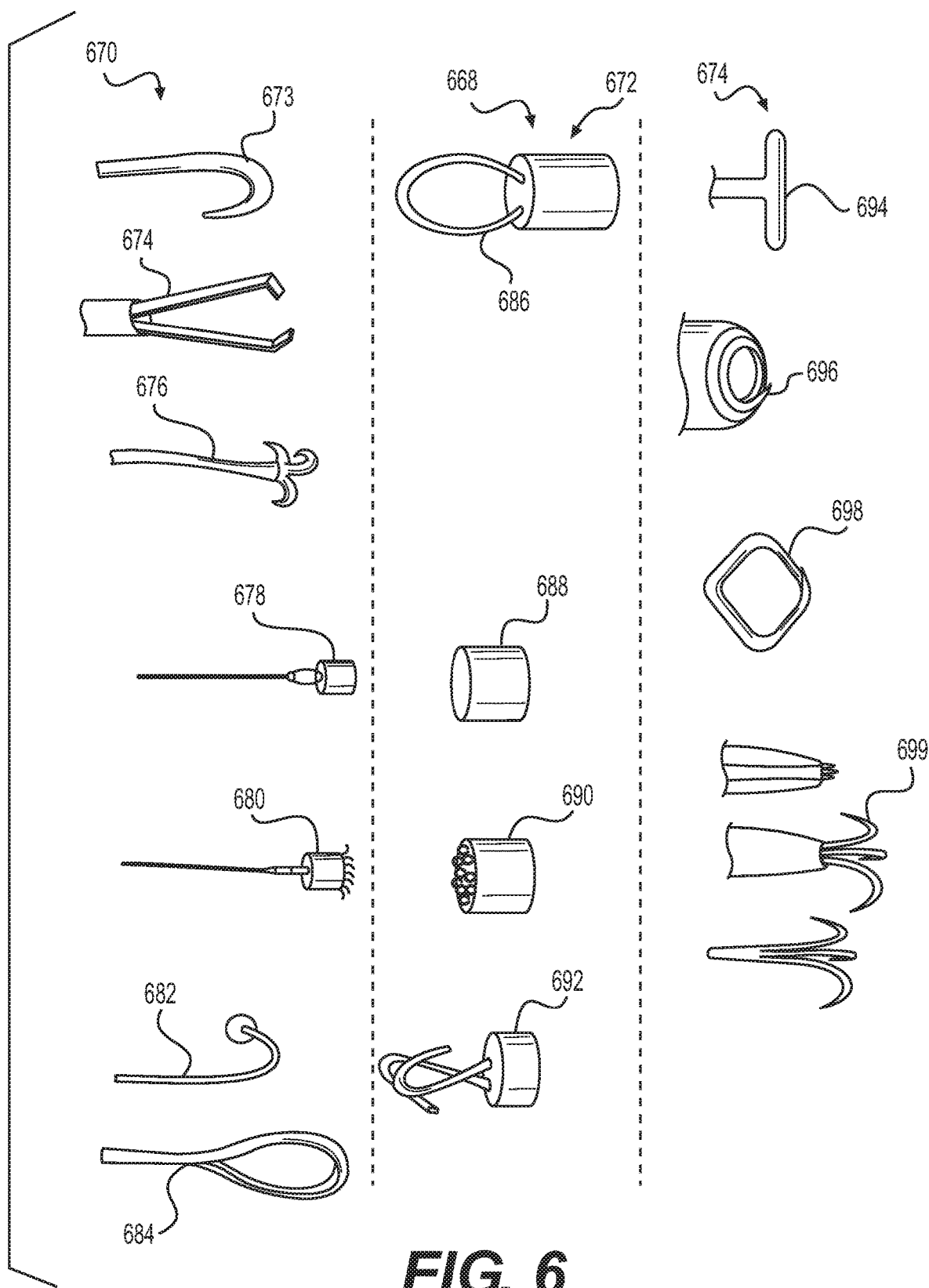
FIG. 6 shows exemplary engagement elements and fasteners arranged in columns, in accordance with aspects of the present disclosure.

FIG. 6 shows an arrangement or table 668 having three columns 670, 672, and 674. Column 670 shows various types of engagement elements including, for example, a single hook 673 having a sharp end, a grasping element 674 with jaws, a multi-hook assembly 676 with sharp ends, a magnet 678, a first half 680 of a hook-and-loop fastener, a hook 682 with a bulbous end, and a loop 684. Any of the engagement members in column 670 may be used in systems 100 and 200, in place of engagement elements 146 and 246 of clips 116 and 216, respectively.

Column 672 shows various types of engagement elements that may engage the engagement elements of column 670. Column 672 includes, for example, a loop or eyelet 686 (configured to attach to single hook 673, grasping element 674, and multi-hook assembly 676), a magnet 688 (configured to attract and attach to magnet 678), a second half 690 of the hook-and-loop fastener (configured to attach to first half 680), and angled hooks 692 (configured to attach to hook 682 and loop 684).

Column 674 shows various types of fasteners that may be used to fasten objects to tissue, the fasteners including, for example, a T-tag 694, a coil 696 with a sharpened tip, a ring element 698, and a self-expanding hook assembly 699. Any of the fasteners in column 674 may be used with any of the engagement elements in column 672, to fasten the engagement elements in column 672 to tissue. The assembly of the fastener from column 674 and the engagement element from column 672 may be used in systems 100, 200, and 300 as anchors 108, 110, 208, 210, 308, and 310, respectively. It also is contemplated that any of the fasteners in column 674 may be used in systems 100 and 200 to fasten anchors 112 and 212 to target areas 104 and 204, respectively. The listing in table 668 shows exemplary aspects, and is not an exhaustive listing of all possibilities. For example, any of the engagement elements and/or fasteners of systems 100, 200, and 300 may form part of table 668.

Figure 7A:
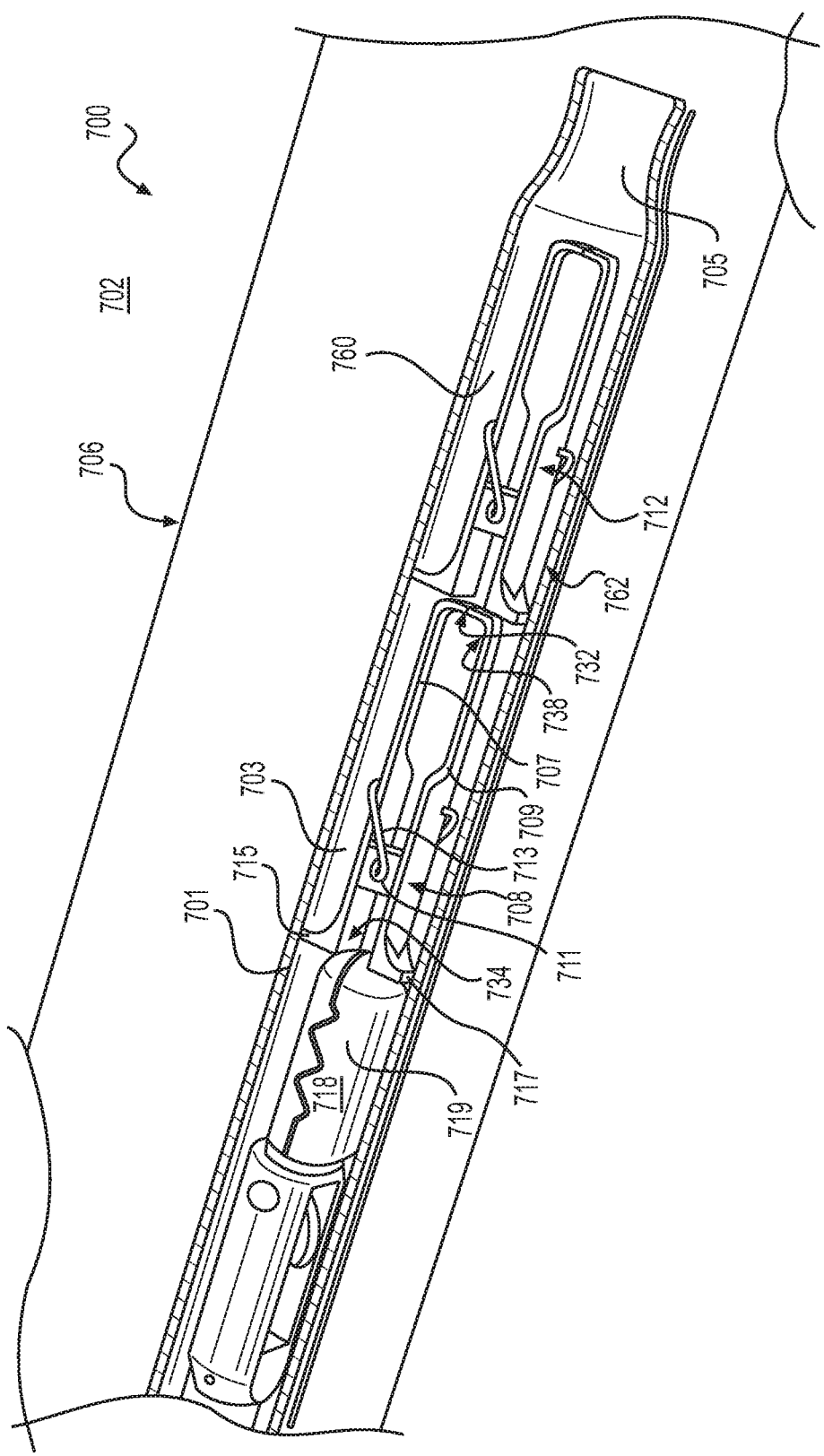
FIGS. 7A-7C show another retraction system in use, in accordance with aspects of the present disclosure.
Figure 7B:
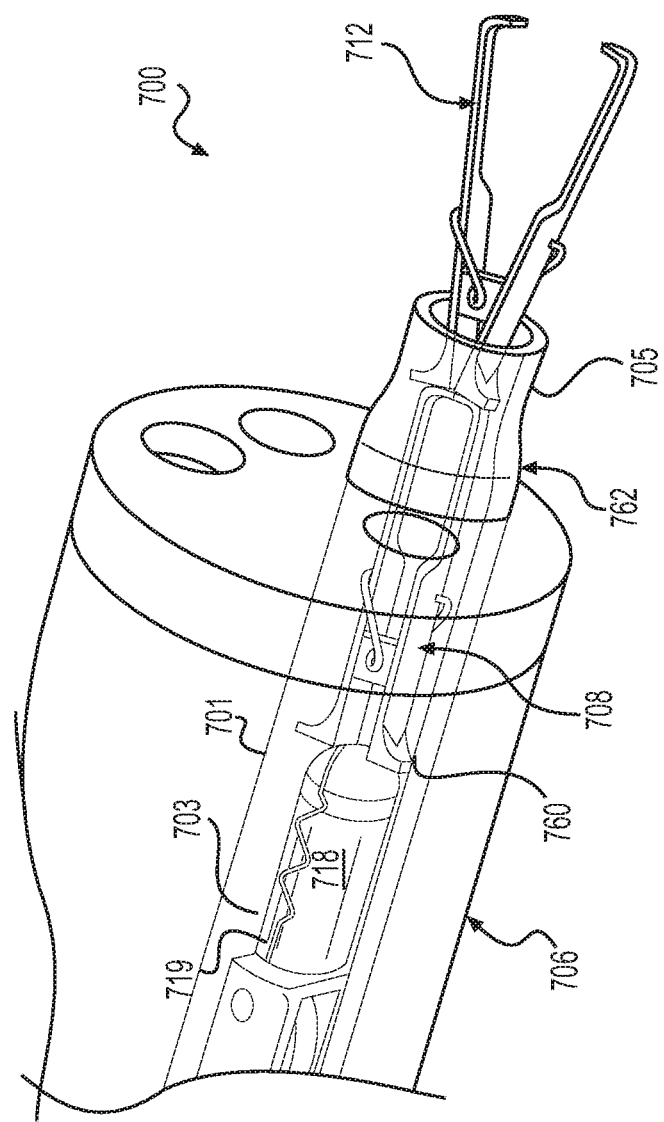
Figure 7C:
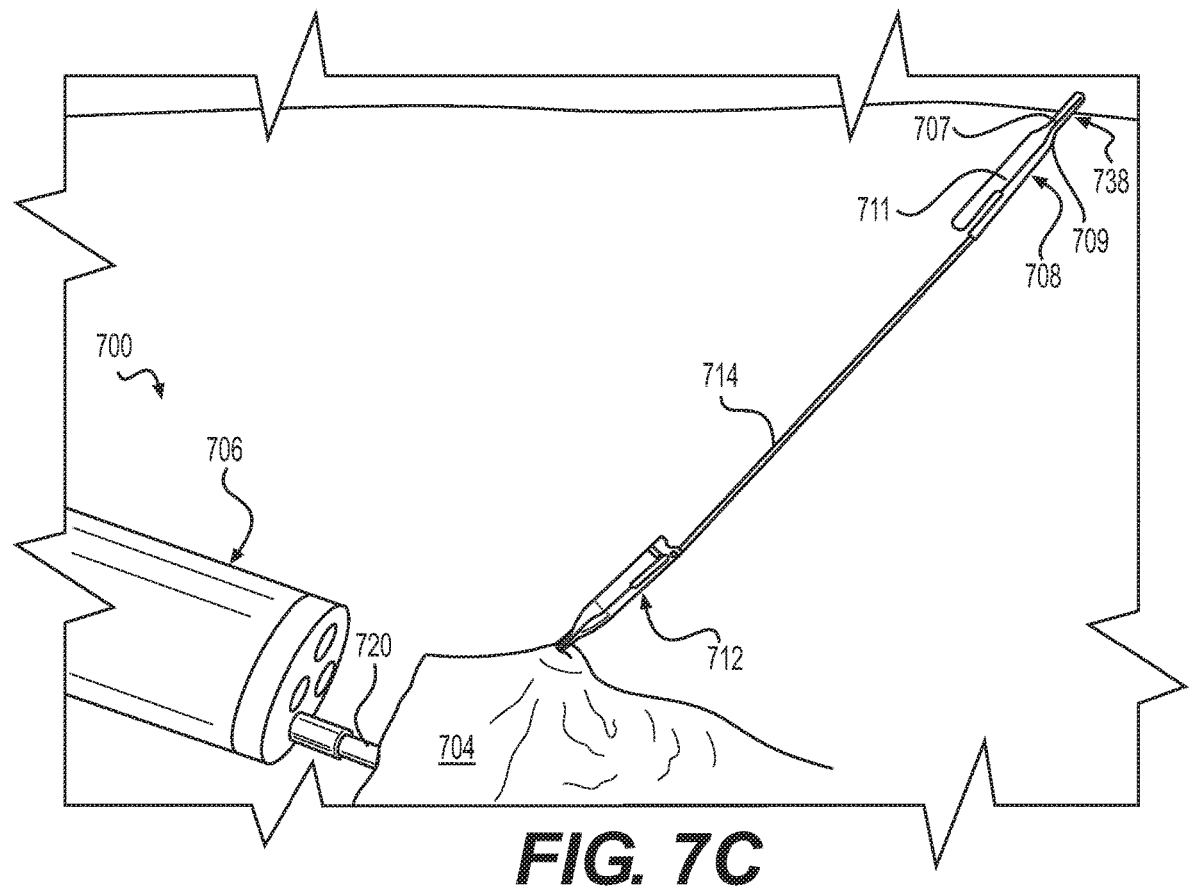

FIGS. 7A-7C show a system 700 for retracting tissue 702. Tissue 702 may include, for example, an area 704 targeted for removal, such as an area with a lesion. System 700 may include an introducer 706 for providing access to tissue 702. Introducer 706 may deploy anchors 708 and 712 to engage a portion of tissue 702 opposing or otherwise facing target area 704, and target area 704 itself, respectively.

FIG. 7A shows system 700 in a delivery configuration for facilitating navigation of the distal end of introducer 706 to target area 704. Anchors 708 and 712 may be received within a holder 762. A positioning instrument 718 also may be received within holder 762. By moving positioning instrument 718 distally, the user may push anchors 708 and 712 distally to deploy anchors 708 and 712. FIG. 7B shows holder 762 extending distally from introducer 706, and anchor 712 being pushed distally out of holder 762, during deployment. The distal end of holder 762 may move anchor 712 into an open configuration as anchor 712 exits from holder 762 (as seen in FIG. 7B). The open anchor 712 may receive target area 704. As anchor 712 separates from holder 762, anchor 712 may close on target area 704, thereby grasping target area 704. A tether 714 may be coupled on one end to anchor 712, and on the other end to anchor 708.

With anchor 712 grasping target area 704, the user may deflect introducer 706 to move holder 762 and clip 708 toward a portion of tissue 702 that may face or otherwise oppose target area 704. The user may use positioning instrument 718 to push anchor 708 out of holder 762 to cause anchor 708 to grasp tissue 702. These movements may impart a tensile force on tether 714, which may pull anchor 712, and thereby retract target area 704, as shown in FIG. 7C. The retraction may be along a vector extending between target area 704 and anchor 712. The movement also may stretch tether 714.

A cutting instrument 720 may be used to cut retracted target area 704. If the cutting affects target area 704 in a way that causes slack to develop in tether 714, the position of anchor 708 may be adjusted by, for example, using positioning instrument 718 to free anchor 708 from tissue 702, reposition anchor 708, and then release anchor 708 such that anchor 708 may engage another portion of tissue 702. This adjustment may provide a user with the ability to utilize different vectors of retraction (e.g., directions and/or magnitudes of retraction) with respect to target area 704. This control over the vector of retraction may provide the user with an enhanced ability to expose and/or visualize the cutting plane the user uses to guide cutting, with cutting instrument 720, for purposes of removing target area 704.

Introducer 706 may, for example, be similar to introducer 106 of system 100. Introducer 706 may include an instrument lumen 701. Instrument lumen 701 is visible in the cutaway view of FIG. 7A; and also in FIG. 7B, where a portion of introducer 706 has been made transparent to show internal features. It is contemplated that other lumens (not shown) may be provided for lighting, imaging, and/or moving material.

Holder 762 may be slidable within instrument lumen 701 of introducer 706, such that the user may retract holder 762 into instrument lumen 701 during navigation of introducer 706 to target area 704, and extend holder 762 out of the distal end of introducer 706 to facilitate deployment of anchors 708 and 710 onto tissue 702. Holder 762 may have a proximal portion 703 and a distal portion 705. A lumen 760 may extend through proximal and distal portions 703 and 705. Proximal portion 703 may be wider than distal portion 705. Additionally or alternatively, an internal diameter of proximal portion 703 may be greater than an internal diameter of distal portion 705. Thus, lumen 760 may be wider in proximal portion 703 than in distal portion 705. The transition from proximal portion 703 to distal portion 705 may be gradual, such that holder 762 and lumen 760 may taper at the transition.

Anchor 708 may include a fastener 738 that secures to tissue 702, such as a grasping element formed by jaws 707 and 709. Jaws 707 and 709 may be pivotably attached to each other at a fulcrum 711. A biasing element 713, such as a torsion spring member, may engage jaws 707 and 709, to bias jaws 707 and 709 to a closed configuration. As jaws 707 and 709 move to the closed configuration, the distal tips of jaws 707 and 709 at a first end 732 of anchor 708 may move toward each other. If unobstructed, the distal tips of jaws 707 and 709 may move into contact with each other. At a second end 734 of anchor 708, on the other side of fulcrum 711, proximal tips of jaws 707 and 709 may move away from each other as jaws 707 and 709 move to the closed configuration. As jaws 707 and 709 move to the open configuration (e.g., against the biasing force exerted by biasing element 713), the proximal tips of jaws 707 and 709 at second end 734 may move toward each other, and the distal tips 707 and 709 at first end 732 may move away from each. Exerting a force on one or more of jaws 707 and 709, at or near the proximal tips of jaws 707 and 709, may move jaws 707 and 709 to the open configuration, allowing jaws 707 and 709 to receive tissue 702. Removing that force may allow jaws 707 and 709 to move to the closed configuration to fasten to tissue 702. Protuberances 715 and 717, such as sloped protrusions, curved protrusions, ramps, or the like, may be provided at the proximal tips of jaws 707 and 709 to facilitate moving jaws 707 and 709 to the open configuration, as described below. Anchor 712 may be similar to anchor 708. Anchors 708 and 712 may be connected by tether 714.

Prior to deployment, anchors 708 and 712 may be serially arranged in lumen 760 at proximal portion 703 of holder 762. First end 732 of anchor 708 may extend toward the distal end of holder 762, and may engage the second end (e.g., the proximal end) of anchor 712. Second end 734 of anchor 708 may engage the distal end of positioning instrument 718. Lumen 760 at proximal portion 703 may be sized such that anchors 708 and 712 may be in their closed configurations. Alternatively, lumen 760 may be sized such that anchors 708 and 712 may be in a partially open configuration due, for example, to engagement between the inner surfaces of holder 762 and protuberances 715 and 717. Tether 714 may be contained in lumen 760 alongside anchors 708 and 712. Alternatively, one or more of anchors 708 and 712 may be flipped end-to-end in lumen 760.

With introducer 706 at or near target area 704, the user may move positioning instrument 718 distally to push anchors 708 and 712 through lumen 760 from proximal portion 703 of holder 762 to distal portion 705. With continued distal movement, positioning instrument 718 may begin to push anchor 712 out of holder 762. As the second end of anchor 712 reaches the transition between proximal portion 703 and distal portion 705 of holder 762, the protuberances on anchor 712 may engage the interior surface(s) of holder 762 due to the reduction in width of holder 762 at distal portion 705. This engagement may exert a compressive force on the proximal tips of the jaws of anchor 712, thereby causing the distal tips of the jaws to move away from each other (FIG. 7B) to receive target area 704. Continued distal movement of positioning instrument 718 may move anchor 712 entirely out of holder 762. As the protuberances on anchor 712 disengage from holder 762, the biasing element of anchor 712 may force the jaws of anchor 712 into the closed configuration, thereby fastening the jaws to target area 704. By these steps, anchor 712 (and anchor 708) may automatically open and close during deployment due to its interactions with holder 762.

The user may move introducer 706 to a position on tissue 702 opposing or otherwise facing target area 704. Due to the connection between anchor 708 (still in holder 706) and anchor 712, via tether 714, this movement may retract target area 704. With the desired vector of retraction achieved, the user may deploy anchor 708 onto tissue 702 in a manner similar to how anchor 712 was deployed onto target area 704, to fix the vector of retraction (see FIG. 7C). The user then may remove holder 762 from instrument lumen 760.

With target area 704 retracted, the user may cut target area 704 with cutting instrument 720 (which may be similar to any of the aforementioned cutting instruments in this disclosure). During cutting, target area 704 may form a flap that may be drawn toward anchor 708 by tension and/or biasing forces in tether 714. This may lead to a reduction in the retraction force on target area 704. In order to increase the retraction force, the user may withdraw cutting instrument 720, and reintroduce positioning instrument 718. The user may extend positioning instrument 718 out of introducer 706. Positioning instrument 718 may include a grasping element 719, such as forceps jaws. The user may exert a compressive force on the proximal tips of jaws 707 and 709, to move anchor 708 to the open configuration, so that tissue 702 is released. Positioning instrument 718 and/or introducer 706 may move anchor 708 to another location on tissue 702 that may exert a different retracting force on target area 704. The user may then return to cutting target area 704. This process may be repeated until target area 704 is removed.

Other variations are contemplated. For example, a plurality of tethers 714 may be used. Each of the tethers 714 may be coupled at their first ends to the same anchor 712. Each of the tethers 714 may have their own anchor 708 at their second end. Each of the tether-anchor pairings may be attached to a different location of tissue 702, thus imparting multiple retraction forces with different vectors on target area 704.

Alternatively, multiple anchor-tether-anchor assemblies (e.g., similar to the assembly of anchor 708, tether 713, and anchor 712) may be used to retract target area 704. For example, one anchor-tether-anchor assembly may be used to initially retract target area 704 during a first cutting phase. Once slack develops in that anchor-tether-anchor assembly, and the desired amount and/or direction of retraction is not provided, another anchor-tether-anchor assembly may be deployed to increase the amount and/or change the direction of retraction. The anchor-tether-anchor assemblies may be identical, or may have one or more differences. For example, one may have a shorter tether, different tether construction, and/or a different type of anchor.

Alternatively, tether 714 may be omitted. Anchors 708 and 710 may be deployed separate from each other to engage tissue without necessarily being used for tissue retraction. For example, anchors 708 and 710 may be used as clips for closing apertures in tissue, positioning tissue, pinching blood vessels, or performing any other suitable task.

Figure 8:
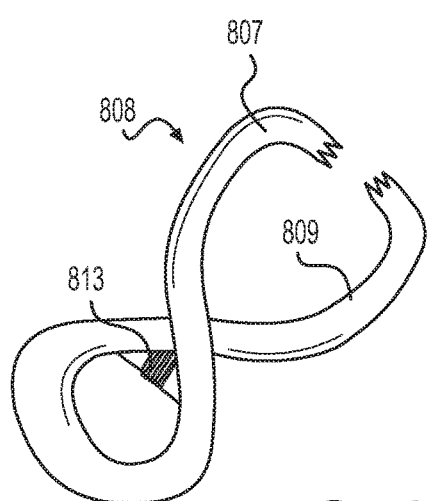
FIG. 8 shows an anchor, in accordance with aspects of the present disclosure.
Figure 9:
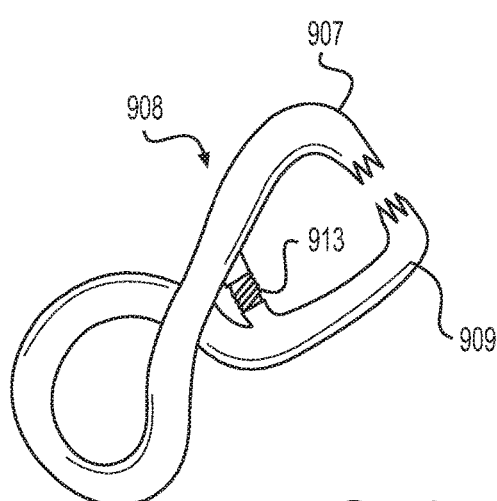
FIG. 9 shows another anchor, in accordance with aspects of the present disclosure.

FIGS. 8 and 9 show anchors 808 and 908. Either of anchors 808 and 908 may be used in place of anchors 708 and 712 of system 700. Anchors 808 and 908 may include integral jaws 807 and 809, and 907 and 909, respectively, forming figure eights.

With respect to anchor 808, a biasing element 813 may engage opposing surfaces of a proximal portion of anchor 808. Biasing element 813 may include, for example, a compression spring. In FIG. 8, biasing element 813 is shown in a partially compressed state, indicative of how biasing element 813 would look when a compressive force is exerted on the proximal portion of anchor 808. In the absence of the force, the distal tips of jaws 807 and 809 may move toward each other and/or into engagement.

With respect to anchor 908, a biasing element 913 may engage opposing surfaces of a distal portion of anchor 908. Biasing element 913 may include, for example, a tension spring. In FIG. 9, biasing element 913 is shown in a partially stretched state, indicative of how biasing element 913 would look when a compressive force is exerted on the proximal portion of anchor 908. In the absence of the force, the distal tips of jaws 907 and 909 may move toward each other and/or into engagement.

Figure 10:
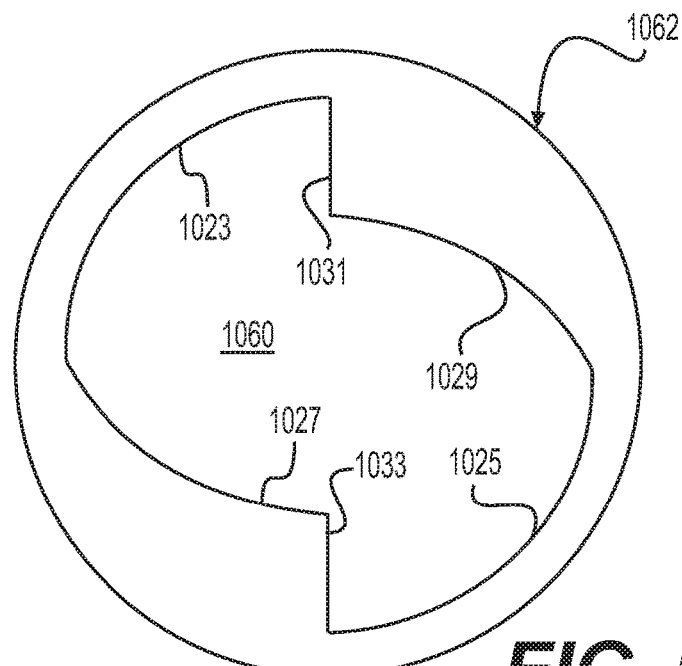
FIG. 10 is an end view of another holder, in accordance with aspects of the present disclosure.

FIG. 10 shows a distal end view of a holder 1062. A lumen 1060 is show within holder 1062. Holder 1062 may include interior surface regions at its distal end that have different internal diameters. For example, the interior surface of holder 1062 may include opposing regions 1023 and 1025. Opposing regions 1023 and 1025 may be equally spaced from a central longitudinal axis of holder 1062. The interior surface of holder 1062 also may include opposing regions 1027 and 1029. Opposing regions 1027 and 1029 may gradually slope toward the central longitudinal axis of holder 1062. The interior surface of holder 1062 also may include opposing regions 1031 and 1033. Opposing regions 1031 and 1033 may provide a transition between opposing regions 1023 and 1025 and adjacent opposing regions 1027 and 1029. Opposing regions 1031 and 1033 may be substantially coplanar, and/or may be straight sections of the interior surface of holder 1062. The portion of the interior surface of holder 1062 having opposing regions 1023 and 1025, 1027 and 1029, 1031 and 1033 may be the distal portion of holder 1062 only. The interior surface of the proximal portion of holder 1062 may be circular, and/or may have an inner diameter similar to that defined between opposing regions 1023 and 1025.

Holder 1062 may be used in place of holder 762 in system 700. Any of anchors 708, 712, 808, and 908 may be positioned in lumen 1060. Regions of the interior surface of holder 1062 may engage the anchors. Using anchor 708 as an example, anchor 708 may be positioned in lumen 1060 in the proximal portion of holder 1062. Anchor 708 may be in its closed configuration, or close to its closed configuration depending on the width of lumen 1060 in the proximal portion of holder 1062. Positioning instrument 718 may move anchor 708 distally, causing the distal portions of jaws 707 and 709 to extend out of holder 1062, and bringing the proximal portions of jaws 707 and 709 into engagement with opposing regions 1023 and 1025. The user may rotate holder 1062 clockwise relative to anchor 708 to bring the proximal portions of jaws 707 and 709 into engagement with opposing regions 1027 and 1029. Continued clockwise rotation of holder 1062 may compress the proximal portions of jaws 707 and 709, due to the decreasing distance between diametrically opposite portions of opposing regions 1027 and 1029. Where the proximal portions of jaws 707 and 709 approach opposing regions 1031 and 1033, anchor 708 may achieve the open configuration. Open jaws 707 and 709 may receive tissue (not shown). Continued clockwise rotation of holder 1062 may cause the proximal portions of jaws 707 and 709 to separate from opposing regions 1027 and 1029, and move radially outward alongside opposing regions 1031 and 1033, due to the biasing force exerted on jaws 707 and 709 by biasing element 713. Anchor 708 may move back towards its closed configuration, thereby fastening jaws 707 and 709 onto the tissue. Any of anchors 712, 808, and 908 may be deployed from holder 1062 in a similar manner.

Figure 11:
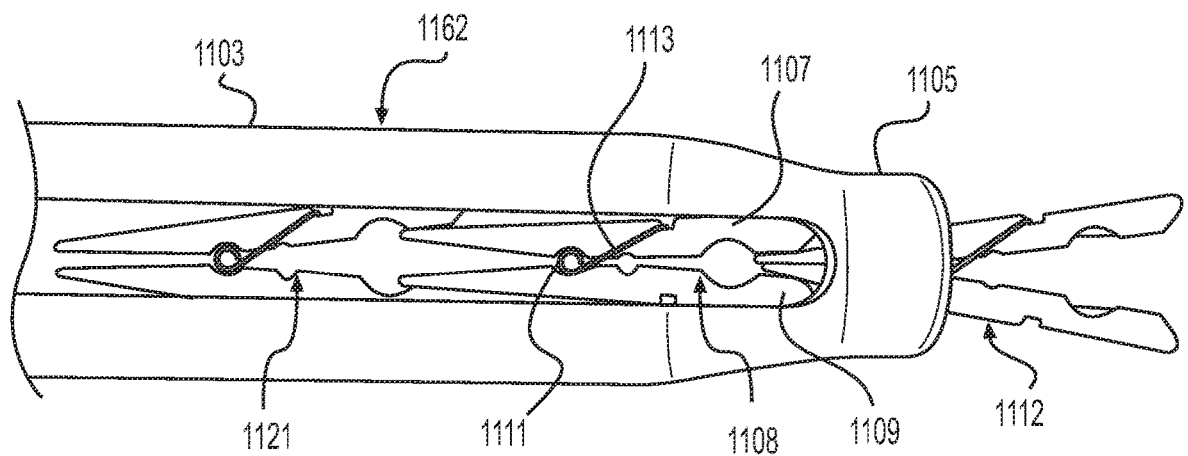
FIG. 11 shows a cutaway view of a holder and anchors, in accordance with aspects of the present disclosure.

FIG. 11 shows a holder 1162 similar to holder 762. For example, holder 1162 may include a proximal portion 1103, a distal portion 1105, and a lumen 1160, wherein a width of lumen 1160 is greater in proximal portion 1103 than in distal portion 1105. In the drawing, a portion of holder 1162 has been cut away to expose the interior of holder 1162 and anchors (e.g., anchors 1108, 1112, and 1121) housed therein. Anchors 1108, 1110, and 1121 may be similar to anchors 708 and 712. For example, anchor 1108 may include jaws 1107 and 1109 that pivot about a fulcrum 1111, and jaws 1107 and 1109 may be biased toward a closed configuration by a biasing element 1113 (e.g., a torsion spring). In the closed configuration, distal tips of jaws 1107 and 1109 may be in contact, or may exert a compressive force on tissue between jaws 1107 and 1109. Exerting a compressive force on proximal tips of jaws 1107 and 1109 may move jaws 1107 and 1109 to an open configuration by overcoming the biasing force exerted by biasing element 1113. Anchors 1112 and 1121 may be similar to anchor 1108.

Prior to deployment from holder 1162, anchors 1108, 1112, and 1121 may be arranged end-to-end, with the distal tips of the jaws of anchor 1121 clamped onto the proximal tips of jaws 1107 and 1109 of anchor 1108. Similarly, the distal tips of jaws 1107 and 1109 of anchor 1108 may be clamped onto the proximal tips of the jaws of anchor 1112.

During deployment, a positioning instrument (not shown, but similar to positioning instrument 718) may be used to push anchors 1108, 1112, 1121 distally through lumen 1160. Anchor 1112 may begin to exit from the distal end of holder 1162. As the distal tips of jaws 1107 and 1109 of anchor 1108 reach the transition between proximal portion 1103 and distal portion 1105 of holder 1162, the reduction in diameter of holder 1162 may cause the interior surfaces of holder 1162 to exert a compressive force on the distal tips of jaws 1107 and 1109 of anchor 1108. This compressive force may act on the proximal tips of the jaws of anchor 1112, thus moving anchor 1112 to its open configuration. Anchor 1112 may receive tissue between its jaws.

As the positioning instrument pushes anchors 1108, 1112, 1121 further distally, the proximal tips of the jaws of anchor 1108 may be compressed by holder 1162 (and the distal tips of the jaws of anchor 1121) at the transition between proximal portion 1103 and distal portion 1105 of holder 1162. Anchor 1108 may release anchor 1112, allowing anchor 1112 to move to its closed configuration to fasten to the tissue. Anchor 1108 may then be ready to receive tissue. This process may be repeated to deploy additional anchors. While three anchors are shown, it should be understood that any suitable number of anchors may be provided in holder 1162. After being deployed, the positioning instrument may be used to exert a compressive force on the proximal tips of any of the jaws of anchors 1108, 1112, 1121, to move the anchor(s) to the open configuration so that tissue is released. The positioning instrument 1118 and/or introducer 1106 may move any of anchors 1108, 1112, 1121 to other locations.

It is contemplated that anchors 1108, 1112, and 1121 may be deployed without being tethered, to engage tissue without necessarily cooperating to retract tissue. For example, anchors 1108, 1112, and 1121 may be used as clips for closing apertures in tissue, positioning tissue, pinching blood vessels, or performing any other suitable task. Alternatively, at least two of anchors 1108, 1112, and 1121 may be linked by a tether (not shown, but similar to tethers 114, 214, and 714) so that two or more of anchors 1108, 1112, 1121 may be used for tissue retraction. While system 1100 has been described above as having holder 1162 with narrowed distal portion 1105, it is contemplated that holder 1062 of FIG. 10 may replace holder 1162. In such an example, relative rotation of holder 1062 relative to anchors 1108, 1112, and 1121 may be used to effect opening and closing of anchors 1108, 1112, and 1121.

FIGS. 12A-12F show a system 1200 for retracting tissue 1202. Tissue 1202 may include, for example, an area 1204 targeted for removal, such as an area with a lesion. System 1200 may include an introducer 1206 for providing access to tissue 1202. Introducer 1206 may facilitate the deployment of anchors 1208 and 1212 onto tissue 1202, such as onto target area 1204 and a portion of tissue 1202 opposing or otherwise facing target area 1204. A tether 1214 that may couple anchors 1208 and 1212 may also be deployed to aid in retracting target area 1204.

Figure 12A:
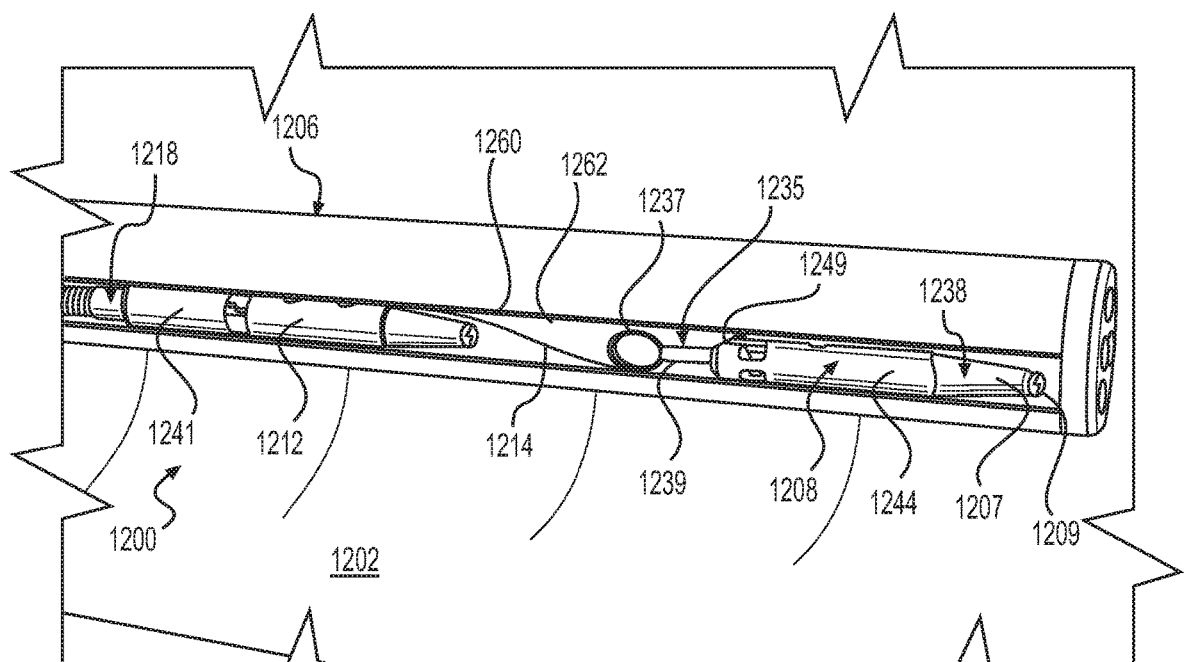
FIGS. 12A-12F show another retraction system in use, in accordance with aspects of the present disclosure.
Figure 12B:
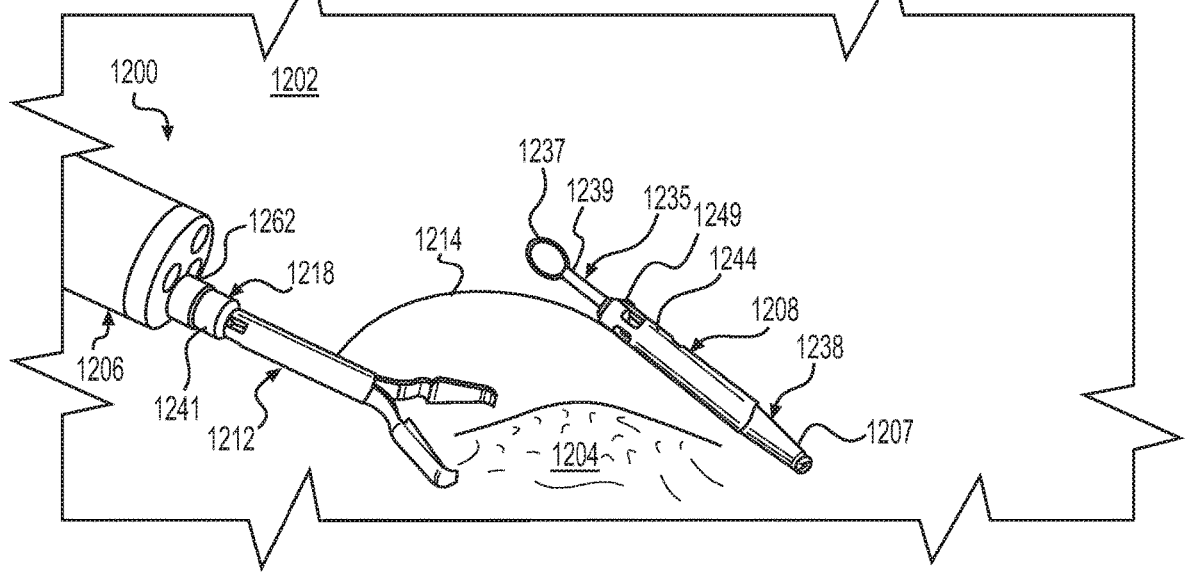
Figure 12C:
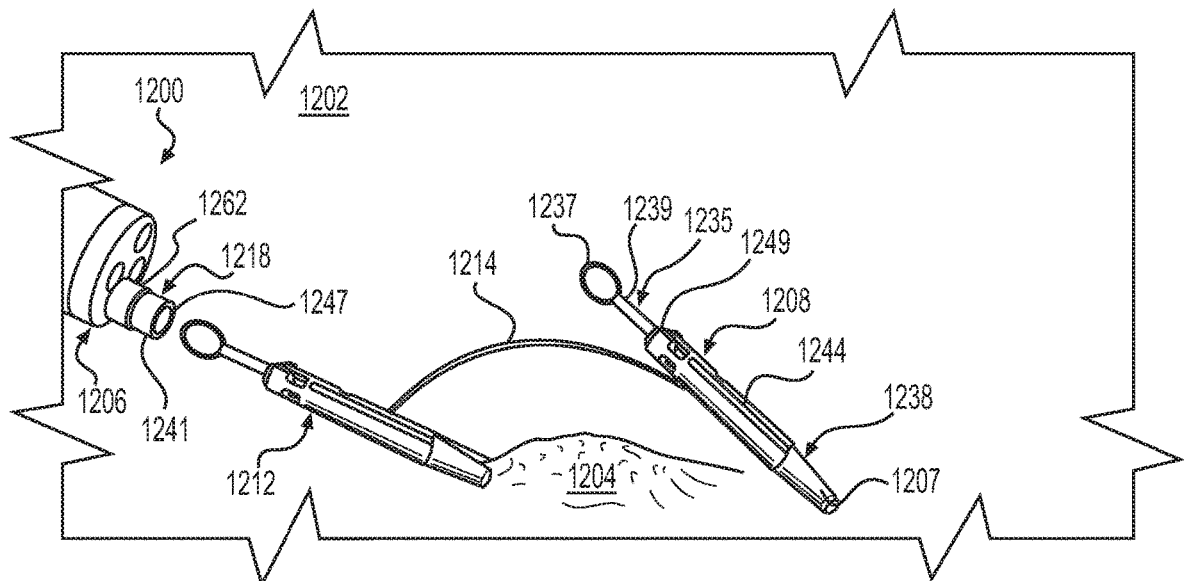

FIG. 12A shows introducer 1206 in a delivery configuration for facilitating navigation of the distal end of introducer 1206 to target area 1204. Anchors 1208 and 1212 may be received within a holder 1262. A positioning instrument 1218 also may be received within holder 1262. Positioning instrument 1218 may be releasably coupled to anchor 1212. By moving positioning instrument 1218 distally, the user may push anchors 1208 and 1212, and tether 1214 distally to eject anchors 1208 and 1212, and tether 1214 out of holder 1262 (see FIG. 12B). Anchor 1208 may be ejected in a closed configuration. Anchor 1212 may initially be ejected in a closed configuration, but once ejected, positioning instrument 1218 may be actuated to move anchor 1212 to an open configuration for receiving target area 1204. Positioning instrument 1218 may be actuated again to move anchor 1212 to a closed configuration to fasten anchor 1212 to target area 1204, as seen in FIG. 12C.

Figure 12D:
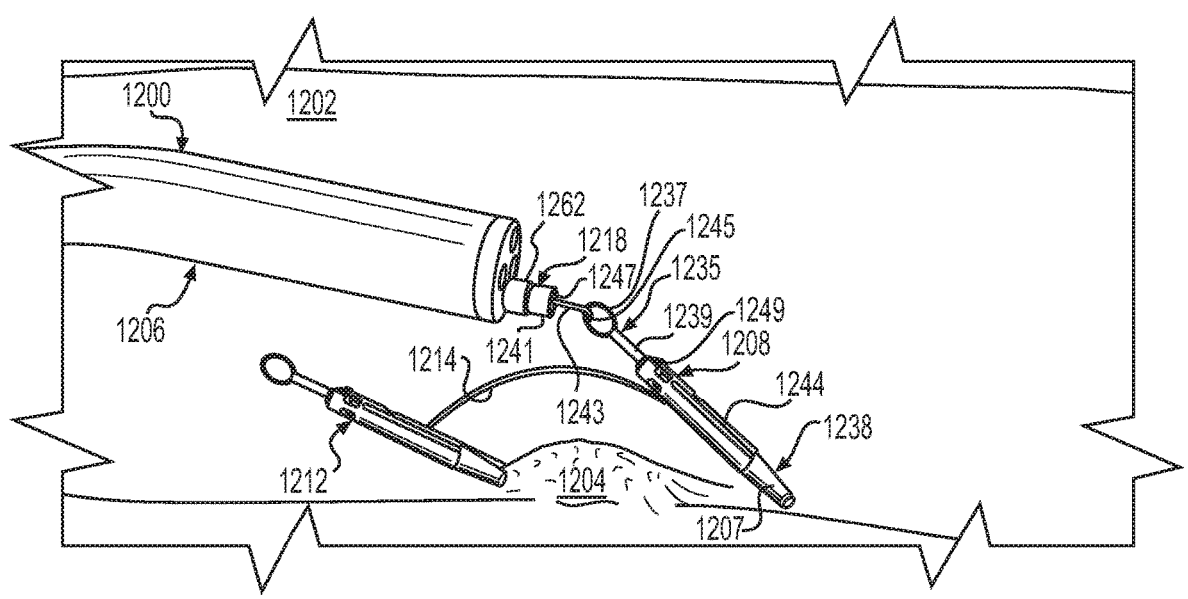
Figure 12E:
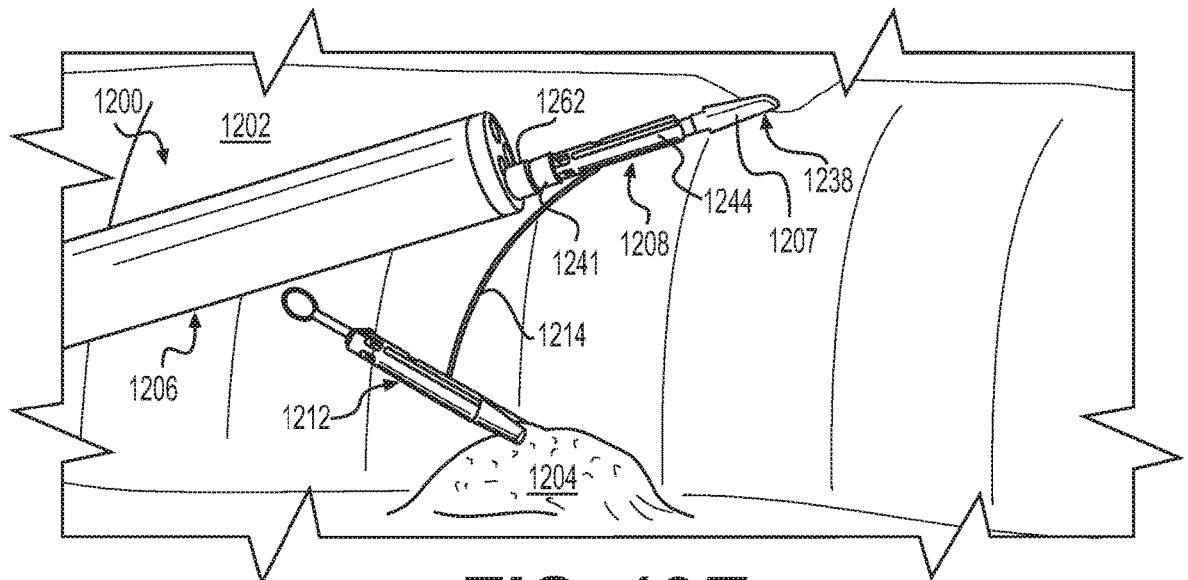

With anchor 1212 fastened to target area 1204, the user may release positioning instrument 1218 from anchor 1212. The user may maneuver introducer 1206 toward anchor 1208, and may releasably couple introducer 1206 to anchor 1208 (see FIGS. 12D and 12E). Using introducer 1206 and positioning instrument 1218, the user may move anchor 1208 to a portion of tissue 1202 opposing or otherwise facing target area 1204. This movement may impart a tensile force on tether 1214, which may pull anchor 1212, and thereby retract target area 1204 (FIG. 12E). When a desired vector of retraction is achieved, the user may actuate positioning instrument 1218 to open anchor 1208. This may allow anchor 1208 to receive tissue 1202, after which positioning instrument 1218 may close anchor 1208 to fasten anchor 1208 to tissue 1202.

Figure 12F:
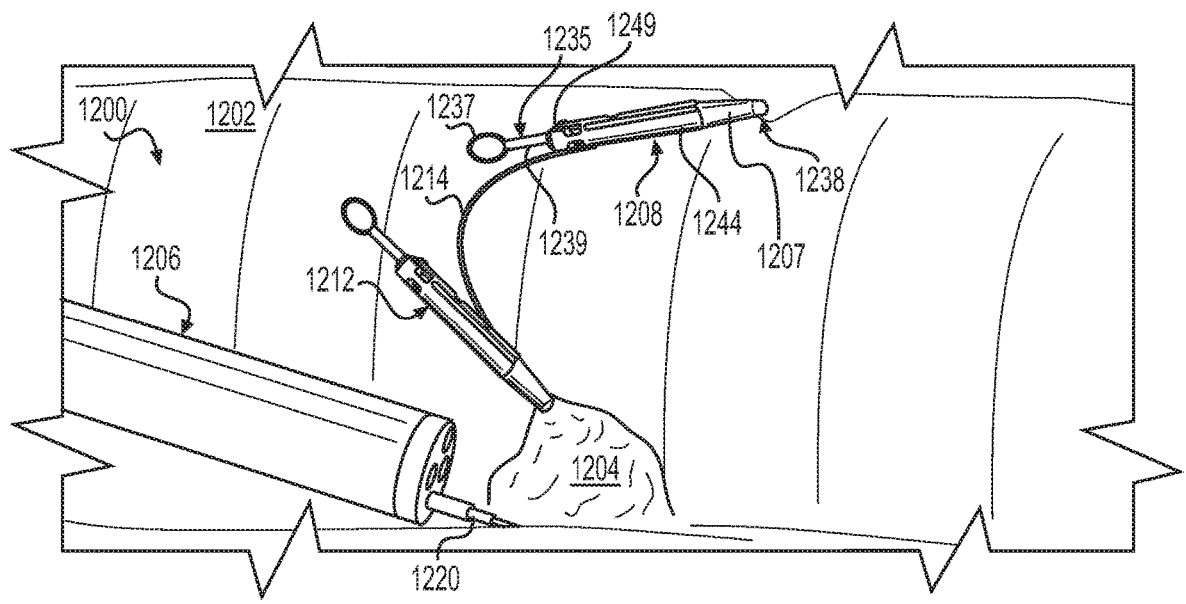

A cutting instrument 1220 (similar to any of the aforementioned cutting instruments in this disclosure) may be used to cut retracted target area 1204 (see FIG. 12F). If the cutting reduces the tension in tether 1214, such that the retraction of target area 1204 is no longer adequate, the position of anchor 1208 may be readjusted. Readjustment may be accomplished by releasably coupling positioning instrument 1218 to anchor 1208 (see FIG. 12D), actuating positioning instrument 1218 to open anchor 1208 to release tissue 1202, moving anchor 1208 to another position on tissue 1202 at which a new desired vector of retraction is achieved, and actuating positioning instrument 1218 to close anchor 1208 to fasten anchor 1208 to tissue 1202 at the new position. This readjustment may provide a user with the ability to utilize different vectors of retraction (e.g., directions and/or magnitudes of retraction) with respect to target area 1204. This control over the vector of retraction may provide the user with an enhanced ability to expose and/or visualize the cutting plane the user uses to guide cutting, with cutting instrument 1220, for purposes of removing target area 1204. Additionally or alternatively, positioning instrument 1218 may be used to move anchor 1212 from target area 1204 to another target area for retraction and removal of the new target area.

Introducer 1206 may be similar to any of the aforementioned introducers described in this disclosure. Introducer 1206 may include lumens, one of which may be an instrument lumen 1260. Holder 1262 may include a sleeve that may be slidable within instrument lumen 1260 such that the distal end of holder 1262 may be extendable out of introducer 1206 (e.g., during deployment of anchors 1208 and 1212) and retractable into introducer 1206 (e.g., during insertion and maneuvering of the distal portion of introducer 1206 to target area 1204).

Anchor 1208 may include a base 1244. Base 1244 may include a sleeve or capsule having an internal lumen. Anchor 1208 also may include a fastener 1238 that secures to tissue 1202, such as a grasping element formed by jaws 1207 and 1209. Fastener 1238 may extend distally out from the distal end of base 1244. Jaws 1207 and 1209 may have a closed configuration (seen in FIG. 12A) and an open configuration (similar to the open configuration of anchor 1212 in FIG. 12B).

Anchor 1208 also may include an actuation element 1235. Actuation element 1235 may include a loop 1237 and a shaft 1239. Loop 1237 may extend proximally out from the proximal end of base 1244. Loop 1237 may be coupled to fastener 1238 by shaft 1239. Shaft 1239 may extend through base 1244. Jaws 1207 and 1209 may occupy the closed configuration when movement of loop 1237 and shaft 1239 in the proximal direction draws jaws 1207 and 1209 toward base 1244. The distal end of base 1244 may exert a constraining force on jaws 1207 and 1209, thus holding them in the closed configuration. Movement of loop 1237 and shaft 1239 in the distal direction may extend jaws 1207 and 1209 distally away from base 1244, removing the constraining force on jaws 1207 and 1209, and thereby allowing jaws 1207 and 1209 to move to the open configuration. Anchor 1212 may be similar to anchor 1208. Anchors 1208 and 1212 may be connected by tether 1214, which may be similar to tethers 114, 214, 714. Ends of tether 1214 may be attached to the bases of anchors 1208 and 1212. Alternatively, tether 1214 may be omitted. In such an example, anchors 1208 and 1212 may be used as individual redeployable surgical clips.

Positioning instrument 1218 may include a receiver 1241 and a manipulation element 1243. Receiver 1241 may include a sleeve or capsule having a lumen (not shown). Manipulation element 1243 may be movable in proximal and distal directions within the lumen of receiver 1241, such that manipulation element 1243 may be extendable out of the distal end of receiver 1241, and retractable into the distal end or receiver 1241. FIG. 12D shows manipulation element 1243 extended distally out of the distal end of receiver 1241. Manipulation element 1243 may be configured to releasably engage loop 1237 of actuation element 1235 of anchor 1208. For example, manipulation element 1243 may include a bent distal end 1245.

Once bent distal end 1245 engages loop 1237, manipulation element 1243 may be withdrawn into receiver 1241 to proximally pull anchor 1208 to receiver 1241. Initially, loop 1237 and a proximal portion of shaft 1239 may be drawn into receiver 1241. Further withdrawal of manipulation element 1243 may draw base 1244 to receiver 1241, such that receiver 1241 may receive base 1244. The distal portion of receiver 1241 and the proximal portion of base 1244 may include cooperating coupling elements 1247 and 1249 for releasably coupling receiver 1241 and base 1244, allowing receiver 1241 to temporarily acquire base 1244. When coupling elements 1247 and 1249 are engaged, receiver 1241 and base 1244 may be fixed relative to each other. Coupling elements 1247 and 1249 may include any suitable releasable mechanical coupling, such as a snap-fit coupling, a latching arrangement, a magnetic coupling, or the like.

With coupling elements 1247 and 1249 engaged, manipulation element 1243 may extend distally to move loop 1237, shaft 1239, and jaws 1207 and 1209 distally relative to base 1244. This may move jaws 1207 and 1209 to their open configuration, such that anchor 1208 may acquire tissue 1202, and/or release previously acquired tissue 1202. Movement of manipulation element 1243 proximally may move jaws 1207 and 1209 back to their closed configuration to fasten anchor 1208 to newly acquired tissue. After anchor 1208 is fastened to tissue 1202, coupling elements 1247 and 1249 may be released from each other, and manipulation element 1243 may be released from loop 1237. Positioning instrument 1218 may be moved away from anchor 1208, leaving anchor 1208 in place on the tissue. This process may be repeated whenever deployment and/or redeployment of anchors 1208 and 1212 onto tissue is desired.

Figure 13:
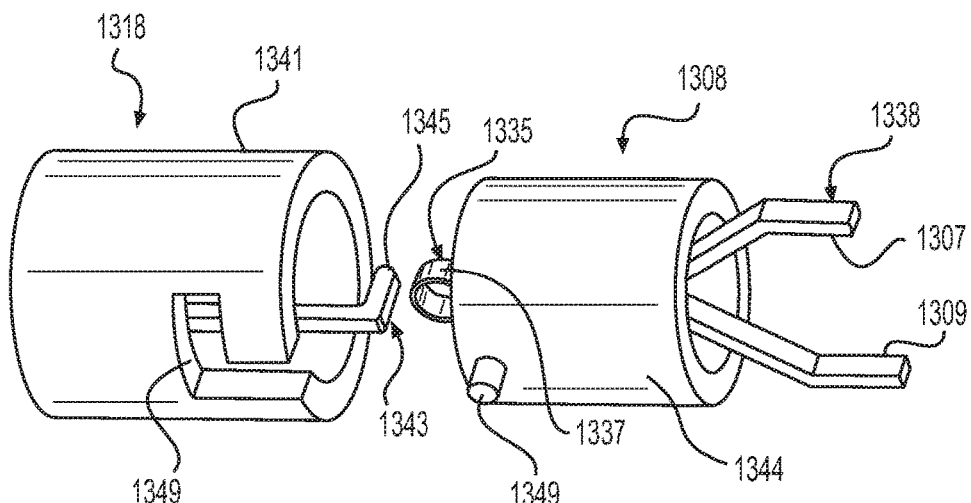
FIG. 13 shows portions of a positioning instrument and an anchor, in accordance with aspects of the present disclosure.

FIG. 13 shows portions of another positioning element 1318 and another anchor 1308, similar in ways to positioning element 1218 and anchor 1208 of system 1200. It is contemplated that the portions of positioning element 1318 and anchor 1308 may be used in place of similar portions of positioning element 1218 and anchor 1208. Positioning element 1318 may include a receiver 1341 and a manipulation element 1343 with a bent distal end 1245. Anchor 1308 may include a fastener 1338 with jaws 1307, 1309; an actuation element 1335 including a shaft (not shown) and a loop 1337; and a base 1344.

Receiver 1341 and base 1344 may include cooperating coupling elements 1347, 1349. Coupling element 1347 may include a groove or channel extending proximally from the distal end of receiver 1341, and laterally, forming an L-shaped cavity. Coupling element 1349 may include a protrusion protruding from an external surface of base 1344. In use, manipulation element 1343 may engage loop 1337, and may draw base 1344 into receiver 1341. Coupling element 1349 may be aligned with coupling element 1347, such that coupling element 1349 may move proximally through coupling element 1347 as manipulation element 1343 moves proximally. By twisting manipulation element 1343, anchor 1308 may be rotated about its central longitudinal axis, causing coupling element 1349 to travel laterally through coupling element 1347. This releasably couples positioning element 1318 to anchor 1308.

With positioning element 1318 releasably coupled to anchor 1308, receiver 1341 and base 1344 may be fixed relative to each other. Manipulation element 1343 may be pulled proximally to close jaws 1307, 1309, for fastening anchor 1308 to tissue. Manipulation element 1343 may be pushed distally to open jaws 1307, 1309, to allow jaws 1307, 1309 to acquire tissue, and/or to release jaws 1307, 1309 from previously acquired tissue for redeployment of anchor 1308.

Figure 14:
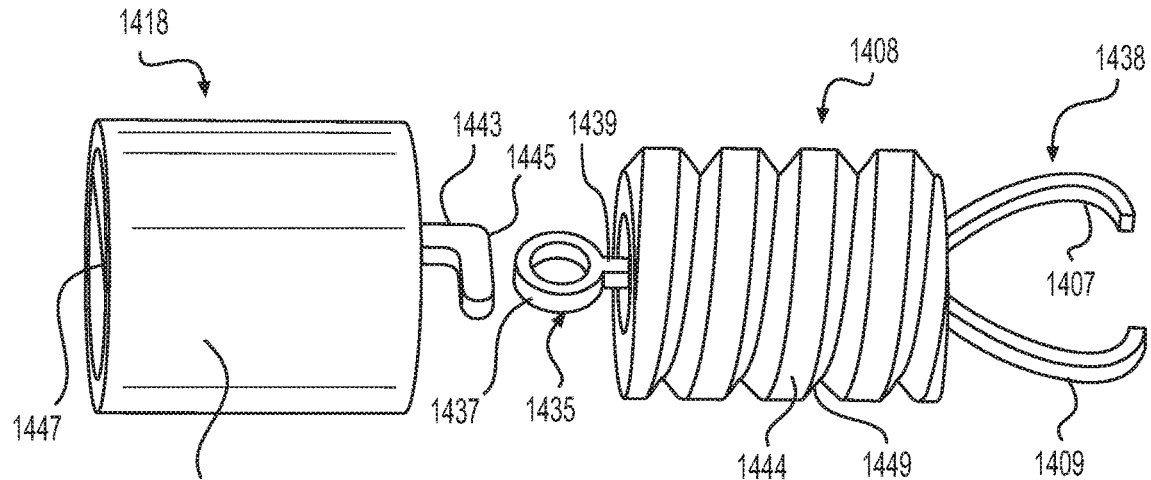
FIG. 14 shows portions of another positioning instrument and another anchor, in accordance with aspects of the present disclosure.

FIG. 14 shows portions of another positioning element 1418 and another anchor 1408, similar in ways to positioning elements 1218 and 1318 and anchors 1208 and 1308 of systems 1200 and 1300, respectively. It is contemplated that the portions of positioning element 1418 and anchor 1408 may be used in place of similar portions of the other positioning elements and anchors. Positioning element 1418 may include a receiver 1441 and a manipulation element 1443 with a bent distal end 1445. Anchor 1408 may include a fastener 1438 with jaws 1407 and 1409; an actuation element 1435 including a shaft 1439 and a loop 1437; and a base 1444.

Receiver 1441 and base 1444 may include cooperating coupling elements 1447 and 1449. Coupling elements 1447 and 1449 may include, for example, mating geometric structures, such as mating screw threads. Coupling element 1447 may include screw threads on an interior surface of receiver 1441. Coupling element 1449 may include screw threads on an exterior surface of base 1444. In use, manipulation element 1443 may engage loop 1437, and may draw the proximal end of base 1444 to the distal end of receiver 1441. By twisting manipulation element 1443, possibly assisted by proximal pulling of manipulation element 1443, anchor 1408 may be rotated about its central longitudinal axis, thereby facilitating engagement of coupling elements 1447 and 1447. Further twisting of manipulation element 1443 may screw anchor 1408 into positioning element 1418. This releasably couples positioning element 1418 to anchor 1408.

With positioning element 1418 releasably coupled to anchor 1408, receiver 1441 and base 1444 may be fixed relative to each other. Manipulation element 1443 may be pulled proximally to close jaws 1407 and 1409, for fastening anchor 1408 to tissue. Manipulation element 1443 may be pushed distally to open jaws 1407 and 1409, to allow jaws 1407 and 1409 to acquire tissue, and/or to release jaws 1407 and 1409 from previously acquired tissue for redeployment of anchor 1408.

Figure 15:
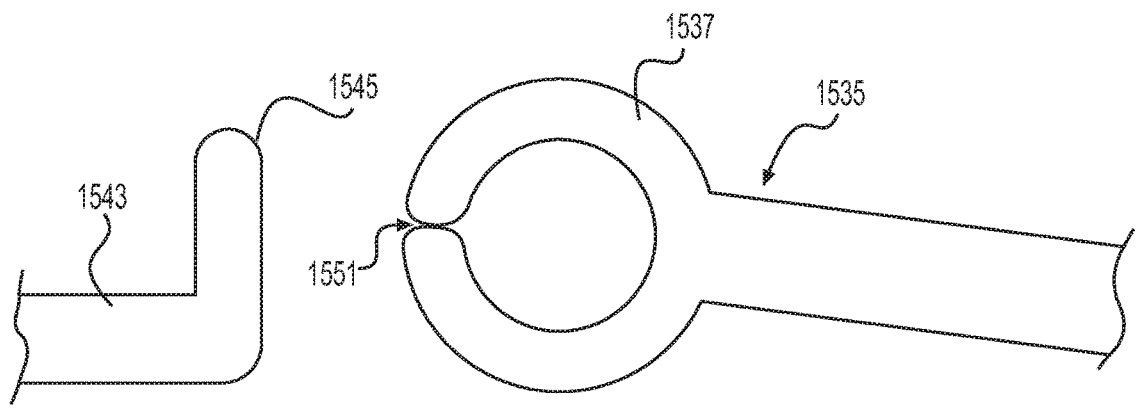
FIG. 15 shows portions of another positioning instrument and another anchor, in accordance with aspects of the present disclosure.

FIG. 15 shows a portion of a manipulation element 1543, and in particular, a bent distal end 1545 of manipulation element 1543. Manipulation element 1543 may be similar in ways to manipulation elements 1243, 1343 and 1443. Bent distal end 1545 may engage a loop 1537 of an actuation element 1535. Loop 1537 may be similar in ways to loops 1237, 1337 and 1437. Loop 1537, however, may have a discontinuity 1551 formed therein. When enough force is applied by bent distal end 1545 at discontinuity 1551, bent distal end 1545 may spread loop 1537 apart, allowing bent distal end 1545 to enter or exit from loop 1537 via discontinuity 1551. Loop 1537 may be used in place of any of loops 1237, 1337, and 1437 to facilitate entry of manipulation elements into the loops, and withdrawal of manipulation elements out of the loops.

Figure 16A:
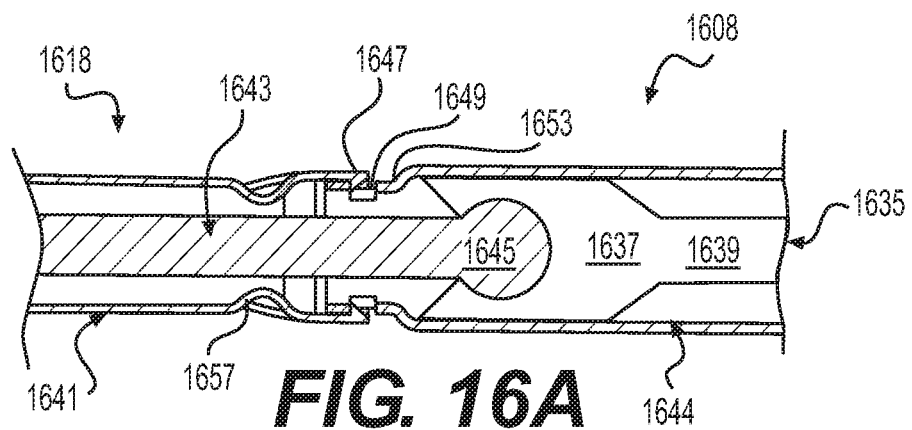
FIGS. 16A and 16B show portions of another positioning instrument and another anchor, in accordance with aspects of the present disclosure.
Figure 16B:
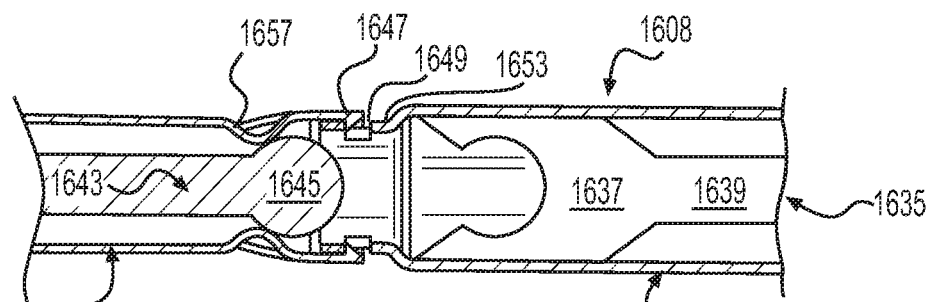

FIGS. 16A and 16B show portions of another positioning element 1618 and another anchor 1608. It is contemplated that portions of positioning element 1618 and anchor 1608 may be used in place of similar portions of any of the other positioning elements described in this disclosure, such as positioning elements 1218, 1318, and 1418. Positioning element 1618 may include a receiver 1641 and a manipulation element 1643 with an enlarged distal end 1645. Enlarged distal end 1645 may include a spherical ball, a circular plate, and/or any other suitable protuberance. Anchor 1608 may include a fastener with jaws (not shown); an actuation element 1635 including a shaft 1639 and a socket 1637; and a base 1644. The fastener may include, for example, aspects of fasteners 1238, 1338, 1438.

Receiver 1641 and base 1644 may include cooperating coupling elements 1647, 1649. Coupling elements 1647, 1649 may include, for example, mating snap-fit elements. Coupling element 1647 may include one or more protrusions an the distal end of the interior surface of receiver 1641. Coupling element 1649 may include one or more indentations or notches on an exterior surface of a proximal end of base 1644, or one or more apertures through one or more sides of the proximal end of base 1644.

FIG. 16A shows coupling elements 1647 and 1649 releasably coupled to each other to fix receiver 1641 relative to base 1644. Enlarged distal end 1645 of manipulation element 1643 also may be releasably coupled to socket 1637 of actuation element 1635. Moving the releasably coupled manipulation element 1643 and actuation element 1635 distally may open the fastener, while moving them proximally may close the fastener. In FIG. 16A, the fastener is closed. Further proximal movement of socket 1637 may be prevented by engagement of the proximal end of socket 1637 with a reduced diameter portion 1653 of base 1644. The closed fastener may be fastened to tissue. To leave anchor 1608 in place on the tissue, manipulation element 1643 may be pulled proximally to pull enlarged distal end 1645 out of socket 1637, as shown in FIG. 16B. Continued proximal pulling of manipulation element 1643 may bring enlarged distal end 1645 into contact with a reduced-diameter portion 1657 of receiver 1641. As enlarged distal end 1645 moves proximally through reduced-diameter portion 1657, enlarged distal end 1645 may force open reduced-diameter portion 1657, which may release coupling element 1647 from coupling element 1649, thereby allowing positioning element 1618 to release from anchor 1608.

In order to remove anchor 1608 from tissue for redeployment, the distal end of receiver 1641 may move toward the proximal end of base 1644. Sloped surfaces of coupling element 1647 may engage the proximal end of base 1644, which may cause coupling elements 1647 to move outwardly and onto the exterior surface of base 1644. Receiver 1641 may move distally relative to base 1644 until coupling element 1647 snaps into engagement with coupling element 1649. Manipulation element 1643 may move to bring enlarged distal end 1645 into engagement with reduced-diameter portion 1657, to help force reduced-diameter portion 1657 outward, thereby facilitating coupling of receiver 1641 to base 1644. Manipulation element 1643 may move distally into engagement with socket 1637 to push socket 1637 distally, thereby opening the fastener. Enlarged distal end 1645 may snap into socket 1637 when pushing socket 1637 distally. In one example, a protrusion, shoulder, or other abutment (not shown) may be provided on the interior surface of base 1644 to engage the distal end of socket 1637, for limiting further distal travel of socket 1637 beyond the point at which the fastener is fully opened. When socket 1637 contacts the protrusion, shoulder, or abutment, forcibly pushing enlarged distal end 1645 against the proximal end of socket 1637 may cause enlarged distal end 1645 to snap into socket 1637.

With the fastener open, anchor 1608 may be released from the one location on the tissue and brought to another location on the tissue. The fastener may be closed onto the tissue at the new location by moving manipulation element 1643 proximally, thereby moving actuation element 1635 proximally, due to receipt of enlarged distal end 1645 into socket 1637. Positioning element 1618 may then be released from anchor per the steps described above. This process may be repeated whenever redeployment is desired.

Figure 17:
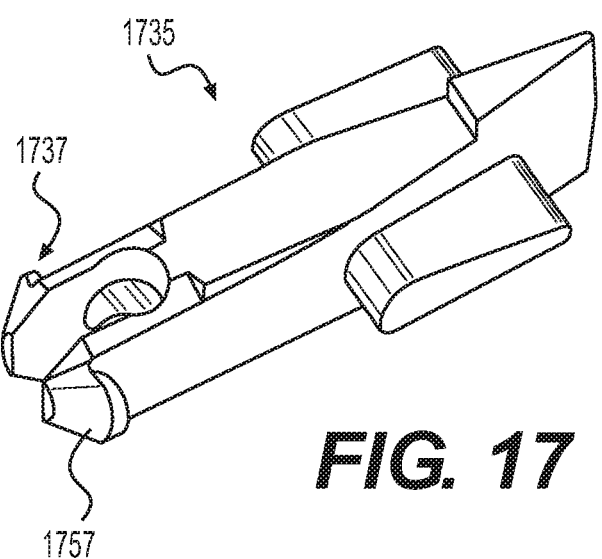
FIG. 17 shows a perspective view of a portion of another anchor, in accordance with aspects of the present disclosure.

FIG. 17 shows a perspective view of a portion of an actuation element 1735 which may be similar to actuation element 1635. Actuation element 1735 may be used in place of actuation element 1635. Actuation element 1735 may include a socket 1737 at its proximal end. The proximal portion of actuation element 1735, however, may extend proximally beyond the proximal end of base 1644, and the rest of actuation element 1735 may be received in base 1644. Lateral protrusions 1757 at the proximal end of socket 1737 may be configured to abut the proximal end of base 1644 when the fastener of anchor 1608 is fully opened. The abutting of lateral protrusion 1757 against the proximal end of base 1644 may hold socket 1737 in place to facilitate insertion of enlarged distal end 1645 of manipulation element 1643 into socket 1737 for use in closing the fastener. Socket 1737 may define a U-shaped recess to facilitate side entry of enlarged distal end 1645 into socket 1737. It also is contemplated that the base of the U-shaped recess may be enlarged to further facilitate side entry of enlarged distal end 1645.

Figure 18:
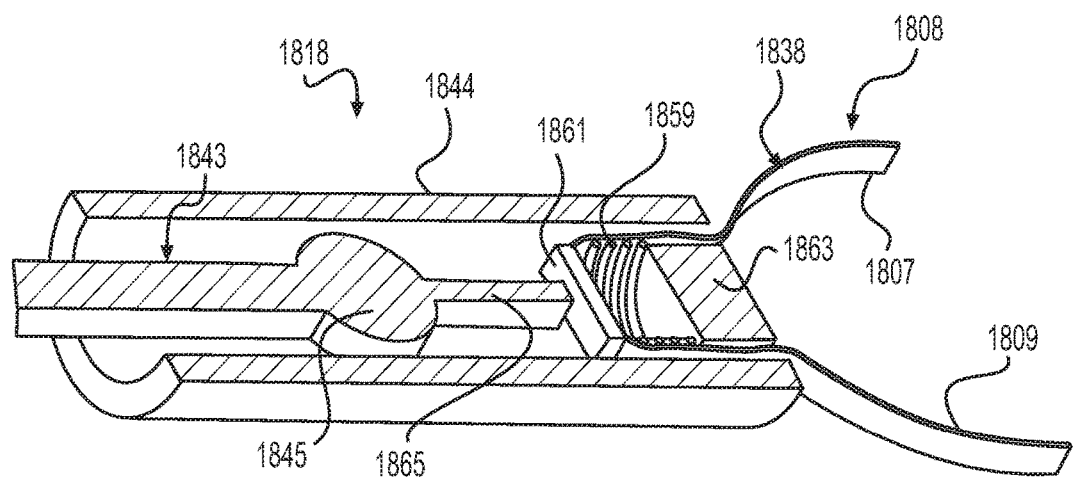
FIG. 18 shows portions of another positioning instrument and another anchor, in accordance with aspects of the present disclosure.

FIG. 18 shows portions of another positioning element 1818 and another anchor 1808, similar in ways to positioning element 1618 and anchor 1608. Anchor 1808 may include a spring-biased fastener 1838 with jaws 1807 and 1809. Fastener 1838 may be spring-biased by a biasing element 1859, which may include a compression spring. A proximal end of biasing element 1859 may engage a base element 1861 at the proximal ends of jaws 1807 and 1809. A distal end of biasing element 1859 may engage a stop 1863 that may be fixed relative to the distal end of a base 1844 of anchor 1808. In the absence of a deforming force acting on biasing element 1859, biasing element 1859 may move base element 1861 away from stop 1863. This may draw jaws 1807 and 1809 toward the distal end of base 1844, and causing jaws 1807 and 1809 to close due to engagement between jaws 1807 and 1809 and the interior surface of the distal end of base 1844 and/or engagement between jaws 1807 and 1809 and the exterior surface of stop 1863.

Positioning element 1818 may be provided with a manipulation element 1843 having an enlarged distal portion 1845 that may be similar to enlarged distal end 1645. Enlarged distal portion 1845 may include a circular plate, a spherical ball, and/or any other suitable form of enlargement. Enlarged distal portion 1845 may be used to engage a receiver (not shown) of positioning element 1818, which may be similar to receiver 1641, to facilitate engagement of a coupling element on the receiver with a coupling element (not shown) on base 1844. The coupling elements may, for example, be similar to coupling elements 1647 and 1649. Enlarged distal portion 1845 also may facilitate disengagement of the coupling elements.

When the coupling elements are engaged, manipulation element 1843 may be pushed distally through base 1844. An extension 1865 extending distally from enlarged distal portion 1845 may engage base element 1861. Extension 1865 may exert a distally-directed force on base element 1861, causing compression of biasing element 1859, and also causing jaws 1807 and 1809 to move to the opened position. Upon removal or reduction of the distally-directed force on base element 1861, biasing element 1859 may move jaws 1807 and 1809 back to the closed position.

FIGS. 19A-19H show a system 1900 for retracting tissue 1902. Tissue 1902 may include, for example, an area 1904 targeted for removal, such as an area with a lesion. System 1900 may include an introducer 1906 for providing access to tissue 1902. Introducer 1906 may facilitate the deployment of a tether 1914 through target area 1904, and an anchor 1908 onto a portion of tissue 1902 opposing or otherwise facing target area 1904.

Figure 19A:
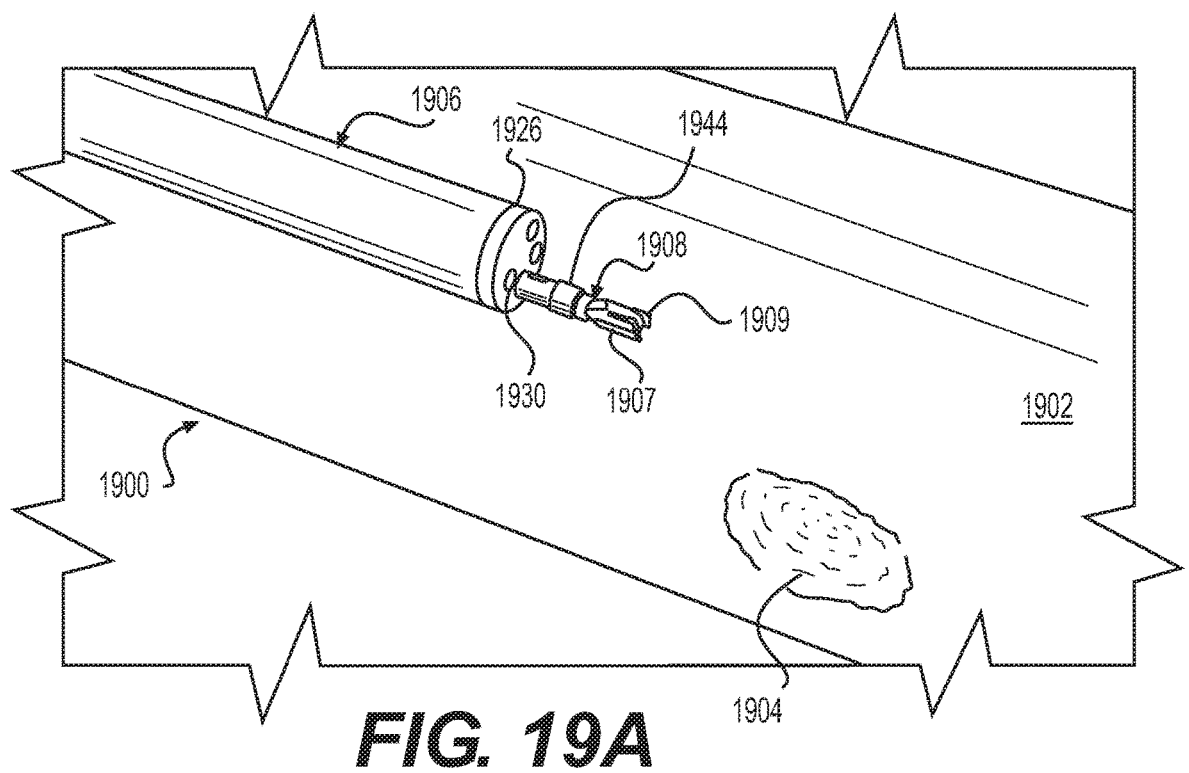
Figure 19B:
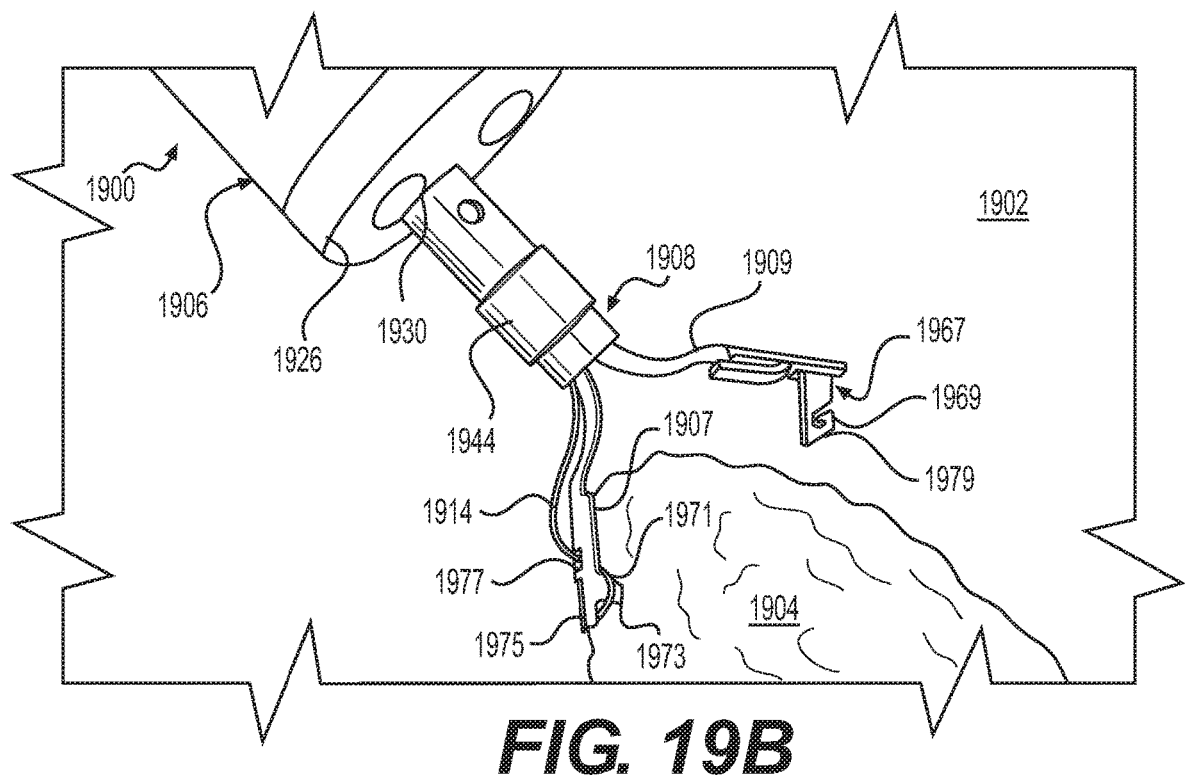
Figure 19C:
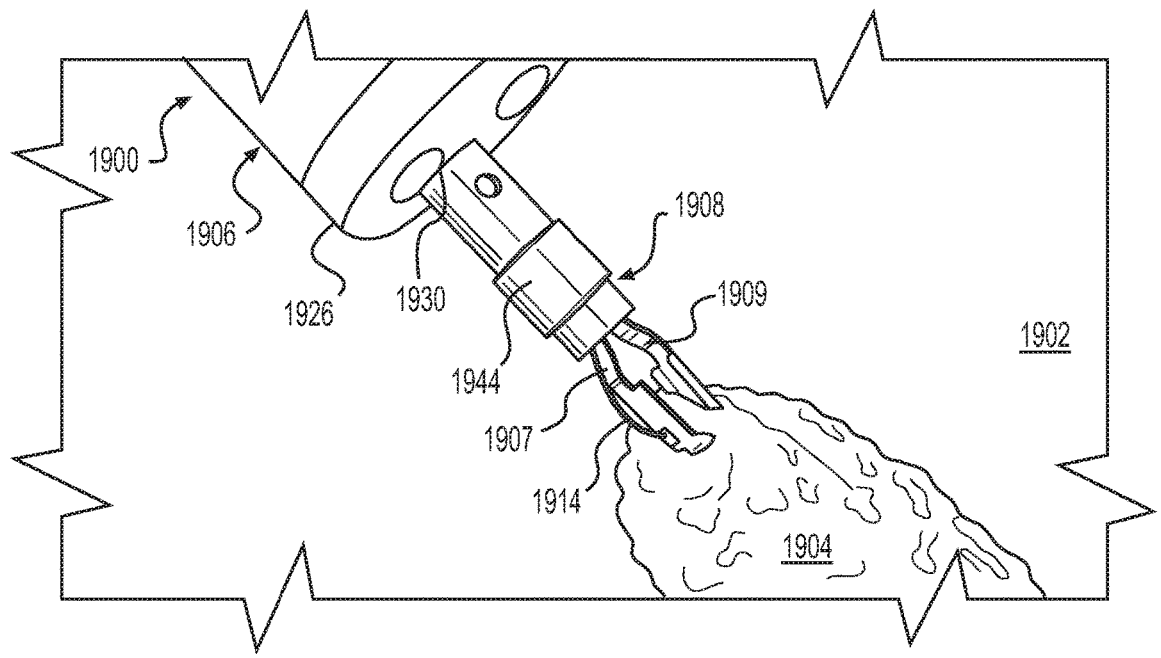
Figure 19D:
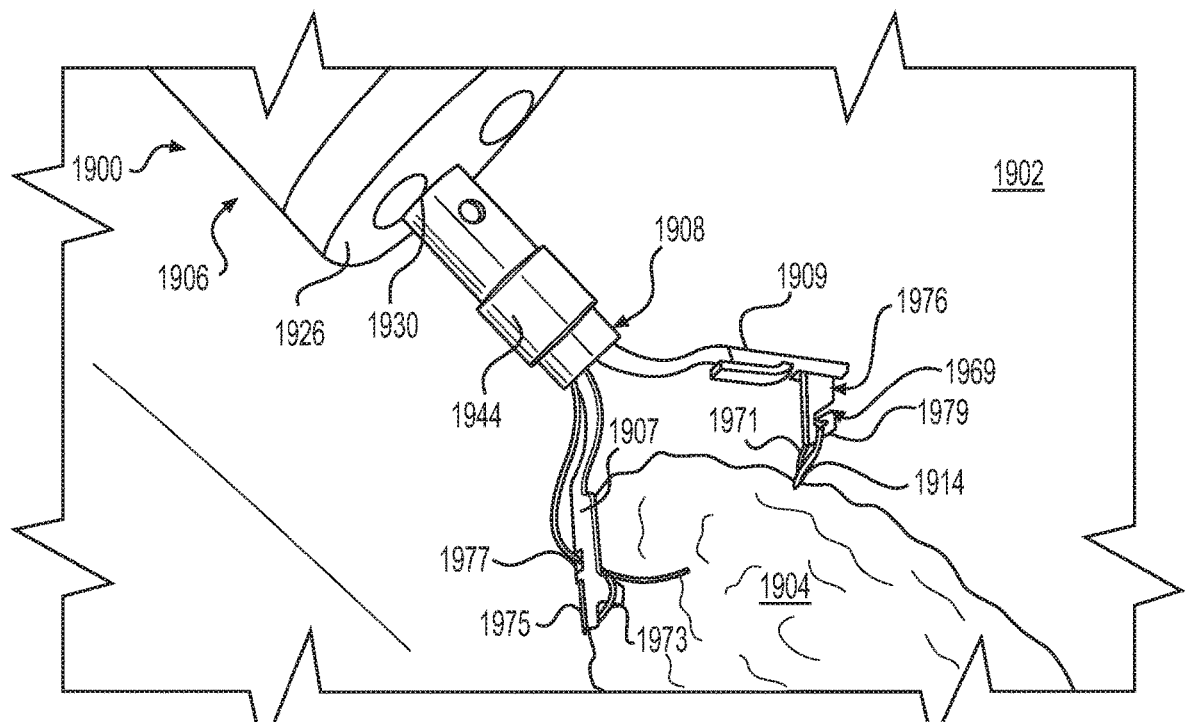
Figure 19E:
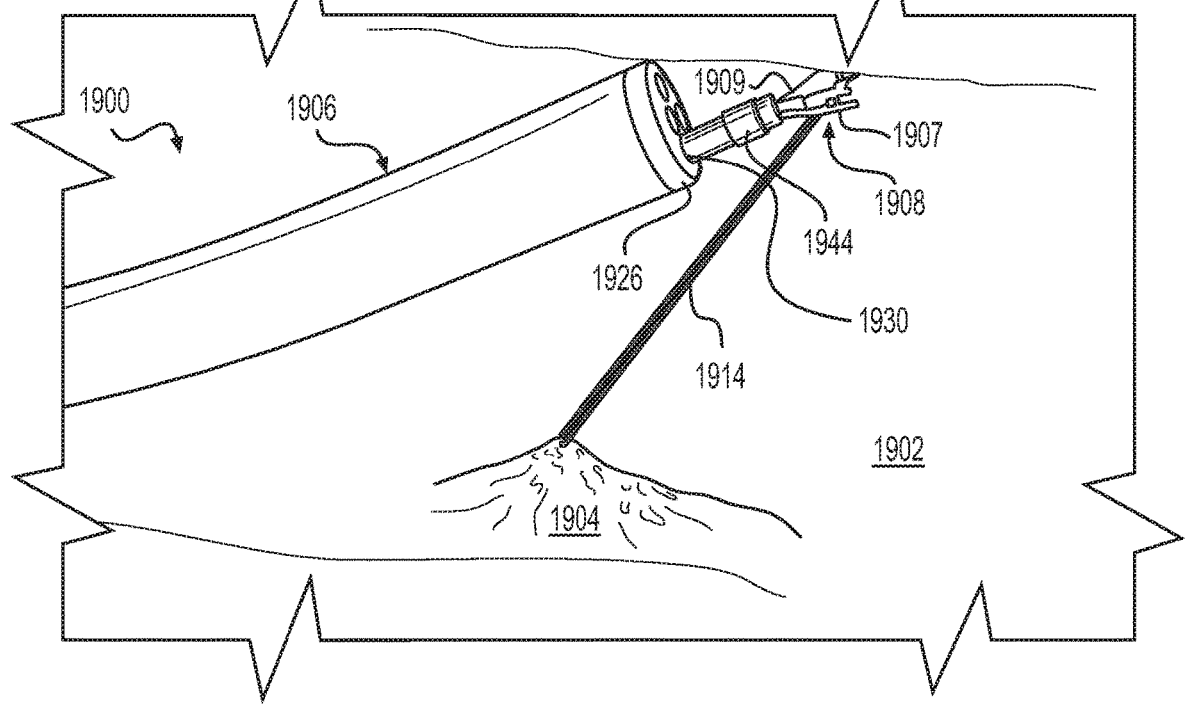
Figure 19F:
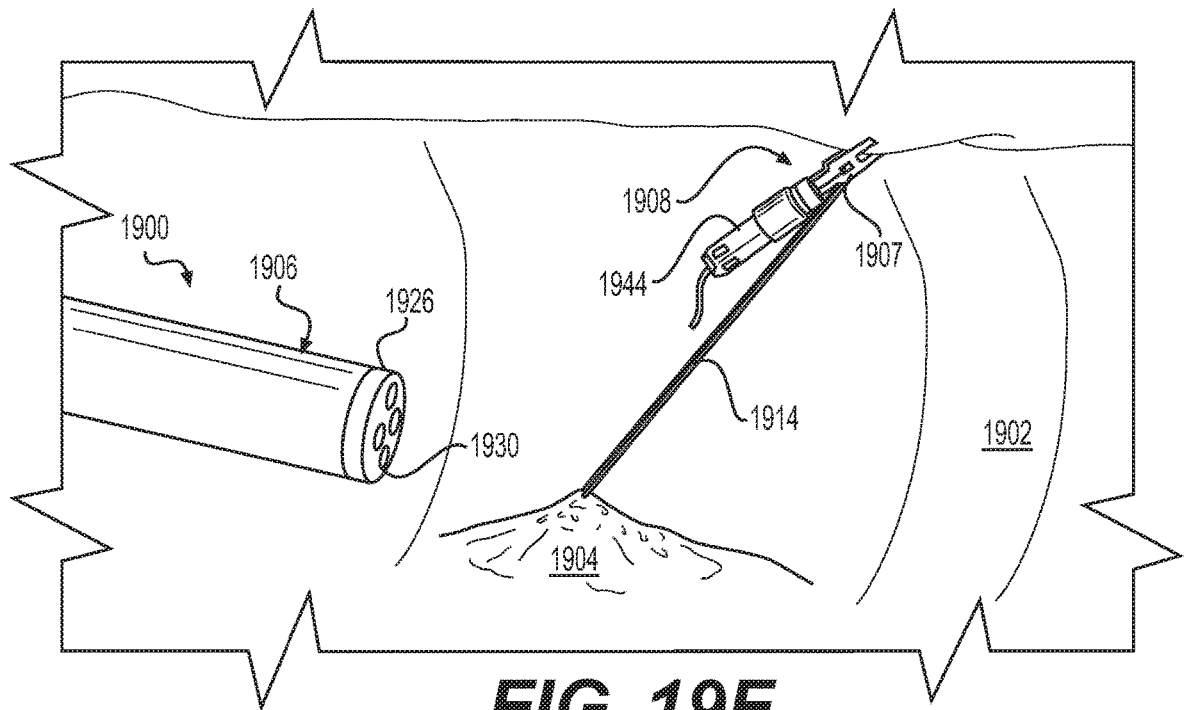

FIG. 19A shows introducer 1906 positioned near target area 1904, and anchor 1908 extended distally from the distal end of introducer 1906. FIG. 19B shows anchor 1908 in an open configuration, with its jaws 1907 and 1909 spread, for receiving target area 1904. Tether 1914 may be secured to jaw 1907. FIG. 19C shows anchor 1908 being moved to a closed configuration to penetrate target area 1904 with jaws 1907 and 1909, and pass tether 1914 through target area 1904. Tether 1914 may be grasped by jaw 1909. FIG. 19D shows anchor 1908 moved back to the open configuration, with tether 1914 now threaded through target area 1904. Anchor 1908 may be opened and closed through actuation of a positioning instrument (not shown).

The user may maneuver introducer 1906 and anchor 1908 to a portion of tissue 1902 opposing or otherwise facing target area 1904. This movement may impart a tensile force on tether 1914, which may pull tether 1914, and thereby retract target area 1904 (seen in FIG. 19E). When a desired vector of retraction is achieved, the user may close anchor 1908 to fasten anchor 1908 to tissue 1202 at a desired location (seen in FIG. 19F).

Figure 19G:
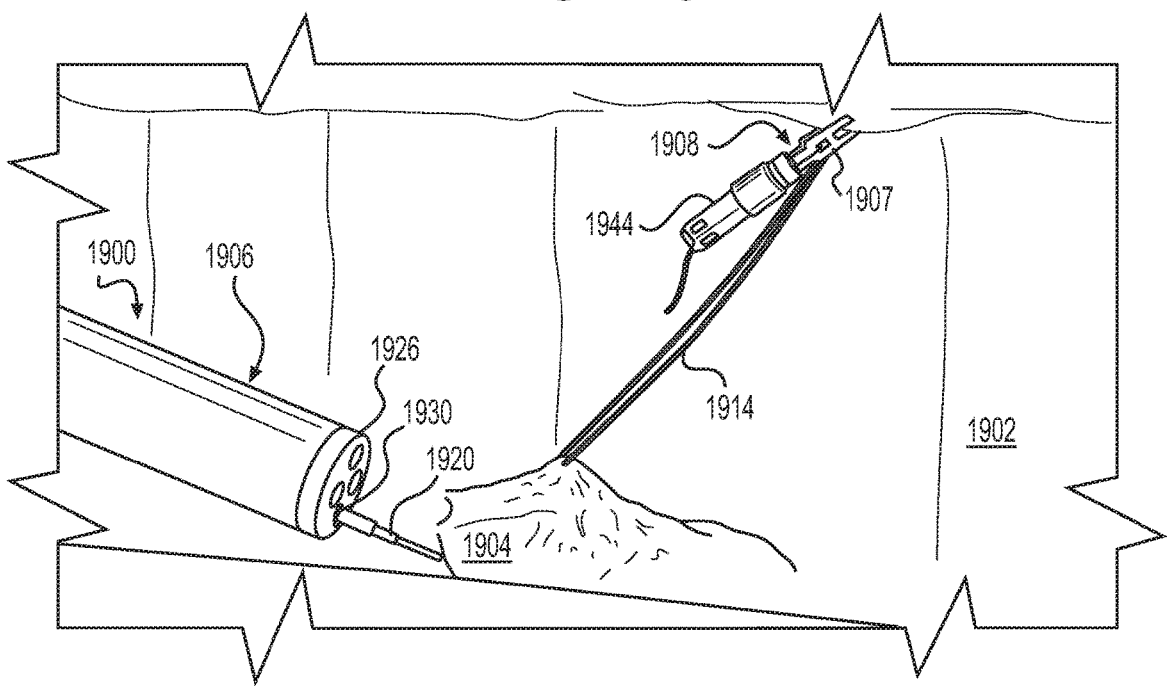

A cutting instrument 1920 (similar to any of the aforementioned cutting instruments described in this disclosure) may be used to cut retracted target area 1904 (see FIG. 19G). If the cutting reduces the tension in tether 1914, such that the retraction of target area 1904 is inadequate, the length of tether 1914 may be adjusted to increase the retraction. Readjustment may be accomplished by grasping a free end of tether 1914 with a forceps or other grasping instrument, and pulling the free end to tighten the portion of tether 1914 coupling anchor 1908 to target area 1904, as shown in FIG. 19H.

Introducer 1906 may be similar to any of the other introducers described in this disclosure. Introducer 1906 may include lumens, one of which may be an instrument lumen (not shown). An end cap 1926 may be provided at the distal end of introducer 1906. End cap 1926 may include ports, one of which may be a port 1930. Port 1930 may open into the instrument lumen. Anchor 1908 may be slidable within the instrument lumen, such that anchor 1908 may be housed within the instrument lumen during delivery, and may be extended out of the instrument lumen via passage through port 1930 to extend distally from the distal end of introducer 1906 for deployment. Movement of anchor 1908 into and out of introducer 1906 may be caused by a positioning instrument (not shown) releasably coupled to anchor 1908. The positioning instrument may, for example, be similar to any of the aforementioned positioning instruments described in this disclosure.

Anchor 1908 may include jaws 1907 and 1909 and a base 1944. Jaws 1907 and 1909 may be movable between open and closed configurations by moving relative to base 1944. For example, jaws 1907 and 1909 may move toward the open configuration when moved distally relative to the distal end of base 1944. Jaws 1907 and 1909 may move toward the closed configuration when moved proximally relative to the distal end of base 1944. The arrangement and operation of jaws 1907 and 1909 and base 1944 may be similar to the arrangement and operation of similar components of anchors 1208, 1210, 1308, 1408, 1608, and 1808. The positioning instrument for operating jaws 1907 and 1909 may be similar to positioning instruments 1218, 1318, 1418, 1618, and 1818.

Tether 1914, which may include a suture, chain, or other suitable structure and/or material, may extend along a portion of jaw 1907 such that a grabbing element 1967 extending laterally inward from jaw 1909 may hook a portion of tether 1914 as anchor 1908 is closed. In use, anchor 1908 may be positioned in the open configuration with jaws 1907 and 1909 over opposite sides of target area 1904 (as seen in FIG. 19B). Anchor 1908 may then be closed so that grabbing element 1967 pierces target area 1904 as jaw 1909 moves toward jaw 1907 (as seen in FIG. 19C). A hook feature 1969 at an end of grabbing element 1967 may interface with jaw 1907 to hook a loop 1971 of tether 1914 extending along first jaw 1907. Anchor 1908 may once again be opened so that grabbing element 1967, with tether 1914 hooked thereto, may be passed through target area 1904, thereby anchoring tether 1914 to target area 1904.

Jaw 1907 may include a notch 1973 along the interior surface of jaw 1907 at the distal end. Jaw 1907 also may include a slot 1975 extending laterally through the distal end thereof in communication with the notch 1973. When loop 1971 of tether 1914 is hooked on notch 1973, a portion of loop 1971 may extend across slot 1975. Grabbing element 1967 may pass through slot 1975, between opposing sides of notch 1973, to hook loop 1971. Jaw 1907 also may include an opening 1977 extending laterally therethrough, with opening 1977 separated from slot 1975 by a distance. Alternatively, jaw 1907 may include a loop, magnet, hook-and-loop fastener, screw, or latch, for mating with a catch, magnet, hook-and-loop fastener, threaded hole, or keeper on tether 1914, to secure tether 1914 to jaw 1907.

A length of tether 1914 may extend through base 1944 of anchor 1908, with a proximal free end of tether 1914 protruding out from the proximal end of base 1944. At its distal end, tether 1914 may be fed through opening 1977 so that a remaining distal length of tether 1914 may extend along the interior surface of jaw 1907. Loop 1971 of tether 1914 may be hooked by opposing sides of notch 1973 so that a portion of loop 1971 extends across slot 1975. Thus, when grabbing element 1967 is passed through slot 1975, grabbing element 1967 may pass through loop 1971 to grab or hook a portion thereof.

Grabbing element 1967 may extend laterally from the interior surface of jaw 1909. Grabbing element 1967 may include hook feature 1969, which may be defined by a J or L-shaped slot. The free end of grabbing element 1967 may have an angled surface 1979 configured so that, as grabbing element 1967 is inserted through slot 1975, loop 1971 may be guided along angled surface 1979 until loop 1971 reaches hook feature 1969 and is received therein. When anchor 1908 is closed, at least a portion of grabbing element 1967 may be received within slot 1975 so that hook feature 1967 hooks loop 1971.

The proximal free end of tether 1914 may extend out of the proximal end of base 1944 (as seen in FIG. 19G) when anchor 1908 is deployed. By pulling the free end, the portion of tether 1914 between target area 1904 and anchor 1908 may be tightened. A one-way mechanism (not shown) may be provided in base 1944. The one-way mechanism may allow tightening of tether 1914, while preventing loosening of tether 1914. The one-way mechanism may include, for example, a ratchet assembly. Tether 1914 may be similar to other tethers described above. Additionally or alternatively, tether 1914 may include grooves and/or protrusions similar to a zip-tie or chain to facilitate one-way movement for tightening. Alternatively, tether 1914 may be omitted, and anchor 1908 may be used individually as a surgical clip.

FIGS. 20A and 20B show a version of system 1900 in which tether 1914 may extend proximally from anchor 1908, into port 1930, through the instrument lumen, and out the proximal end of introducer 1906. The user may adjust retraction on target area 1904 from the proximal end of introducer 1906 by pulling tether 1914. The step of grasping tether 1914 using a forceps or the like may be avoided.

Another difference with FIGS. 20A and 20B is that tether 1914 may not extend through base 1944. As such, the one-way mechanism need not be provided in base 1944. Rather, the one-way mechanism may be provided in port 1930, the instrument lumen, or at the proximal end of introducer 1906, to prevent loosening of tether 1914 between target area 1904 and anchor 1908. As explained above, the one-way mechanism may include a ratchet assembly, zip tie features, or the like. Additionally or alternatively, the one-way mechanism may include a tie down at the proximal end of introducer 1906 to prevent unwanted distal migration of tether 1914.

In FIG. 20A, cutting instrument 1920 may cut target area 1904 in a manner that produces a flap. This may cause slack to develop in the portion of tether 1914 between anchor 1908 and target area 1904. FIG. 20B shows the portion of tether 1914 between anchor 1908 and target area 1904 after being tightened by pulling the proximal end of tether 1914 from the proximal end of introducer 1906.

FIGS. 21A and 21B show a version of system 1900 wherein the retraction vector acting on target area 1904 may be adjusted by deploying an auxiliary anchor 1910. Auxiliary anchor 1910 may be maneuvered by introducer 1906 (or another introducer) into engagement with the portion of tether 1914 between anchor 1908 and target area 1904. Auxiliary anchor 1910, while holding tether 1914, may be fastened to tissue 1902 at another location, thereby adjusting the magnitude and/or direction of the retraction force exerted on target area 1904 by tether 1914 and anchor 1908. Additional auxiliary anchors may be deployed to further adjust the retraction vector. It is also contemplated that auxiliary anchor 1910 may be used to adjust the retraction vector of any of the other aforementioned tethers described in this disclosure.

FIG. 22 shows yet another exemplary version of an auxiliary anchor 2210 that may be used to adjust the retraction vector by engaging tether 1914 and tissue 1902. Auxiliary anchor 2210 may include opposed jaws 2283 and 2285. Jaws 2283 and 2285 may include biasing elements 2287, 2289, such as torsion springs, to bias jaws 2283 and 2285 into closed configurations. Jaws 2283 and 2285 may be linked by a spring member 2291. Spring member 2291 may include a tension spring that can be stretched to exert a retraction force between jaws 2283 and 2285, and material grasped by jaws 2283 and 2285. Opposite ends of spring member 2291 may be pivotably coupled to jaws 2283 and 2285 by swiveling links 2293, 2295. In one example, jaw 2283 may be opened to receive tether 1914, and closed to grasp tether 1914. Jaws 2285 may be fastened to tissue after a desired amount of retraction force is exerted on tether 1914 via jaws 2283 and spring member 2291.

Figure 23A:
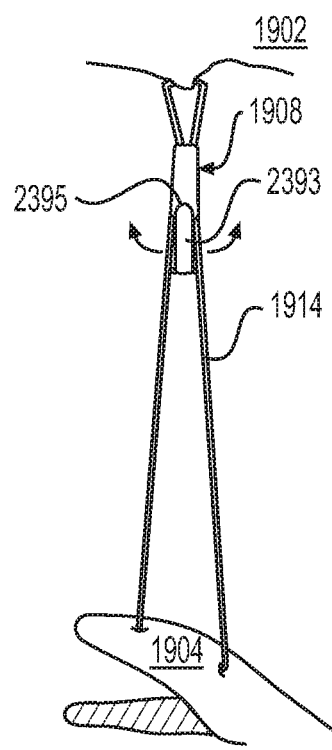
FIGS. 23A and 23B show another version of the retraction system of FIGS. 19A-19H in use, in accordance with aspects of the present disclosure.
Figure 23B:
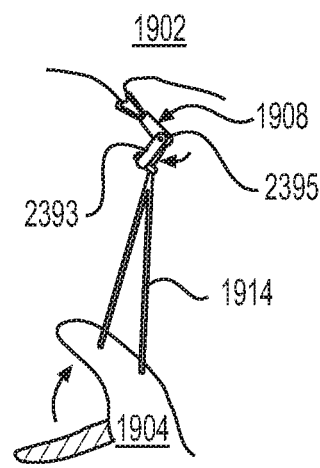

FIGS. 23A and 23B show a version of system 1900 wherein the retraction vector acting on target area 1904 may be adjusted by adjusting an angle of a swivel link 2393 pivotably coupled to base 1944 of anchor 1908 by a hinge 2395. In FIG. 23A, swivel link 2393 may be positioned relative to base 1944 such that their central longitudinal axes are coaxial. Swivel link 2392 may be pivoted relative to base 1944 such that their central axes are angled, as shown in FIG. 23B. A locking mechanism, such as a ratchet assembly or the like, may be provided at hinge 2395 to maintain the angled orientation of swivel link 2392 relative to base 1944. The angling of swivel link 2392 may redirect the direction of retraction force exerted on target area 1904, and may increase the magnitude of the retraction force, to facilitate cutting of target area 1904. It is contemplated that this swivel link connection may be provided between any of the aforementioned tethers and anchors in this disclosure.

Figure 24A:
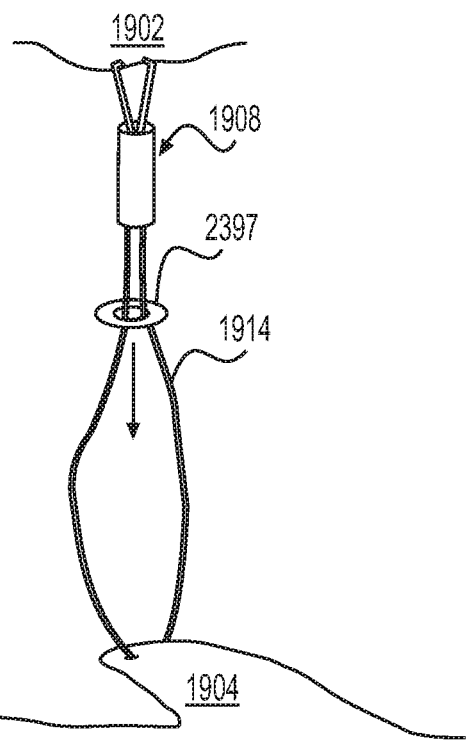
FIGS. 24A and 24B show another version of the retraction system of FIGS. 19A-19H in use, in accordance with aspects of the present disclosure.
Figure 24B:
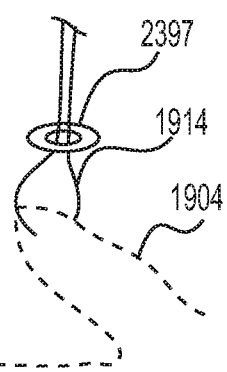

FIGS. 24A and 24B show a version of system 1900 wherein the retraction vector acting on target area 1904 may be adjusted by adjusting a distance between legs of tether 1914 in the portion of tether 1914 that extends between target area 1904 and anchor 1908. The adjustment may be provided using an annular element 2397. The user may slide annular element 2397 down tether 1914 from the position shown in FIG. 24A, toward target area 1904. Continued sliding of annular element 2397 toward target area 1904 to the position shown in FIG. 24B may reduce the length of tether 1914 passing through target area 1904 such that tether 1914 may cinch target area 1904. The cinching may cause target area 1904 to tent upward. It is contemplated that annular element 2397 may be used with any version of system 1900 described in this disclosure.

Figure 25B:
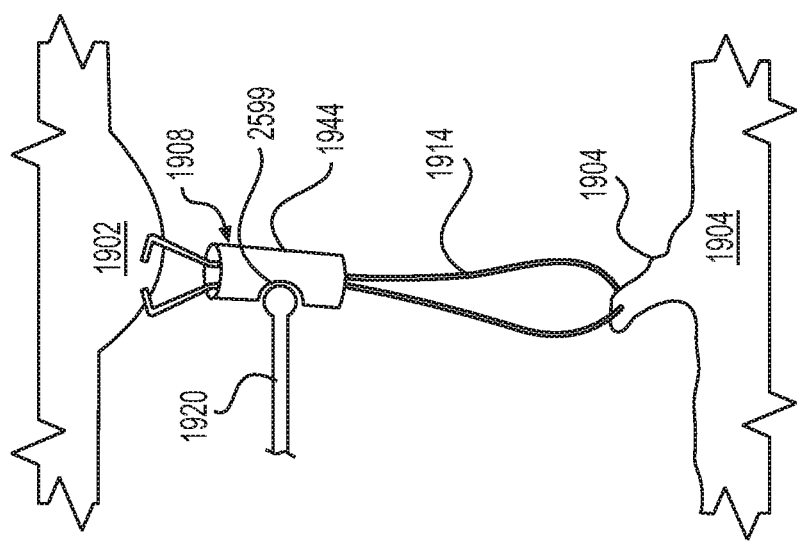
FIGS. 25A and 25B show another version of the retraction system of FIGS. 19A-19H in use, in accordance with aspects of the present disclosure.
Figure 25A:
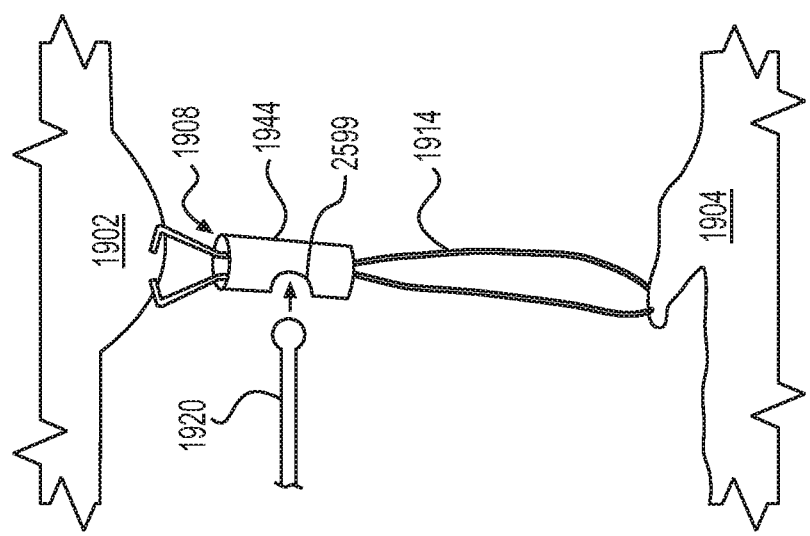

FIGS. 25A and 25B show a version of system 1900 wherein the retraction force exerted on target area 1904 by tether 1914 may be adjusted by heating tether 1914 and/or directing electrical energy into tether 1914. In such an example, tether 1914 may be made using "muscle wire," which may include, for example, a nitinol wire configured to contract when heat or electrical energy is applied. Base 1944 of anchor 1908 may include a port 2599 configured to receive, for example, the distal tip of cutting instrument 1920. Cutting instrument 1920 may supply the energy for contracting tether 1914 via port 2599. FIG. 25A shows tether 1914, and the retraction force exerted on target area 1904, prior to contraction of tether 1914. FIG. 25B shows tether 1914, and the increased retraction force, after contraction of tether 1914. It is contemplated that any of the aforementioned bases and tether arrangements in this disclosure may include muscle wire, and a port for directing energy into the muscle wire, to provide increased retraction through contraction of the muscle wire.

It will be apparent to those skilled in the art that various modifications and variations can be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A method comprising:
   extending a coupling element between a first element engaging a target area of tissue at a first location along the tissue and a second element at a second location along the tissue spaced apart from the first location, the coupling element having a first end coupled to the first element and a second end coupled to the second element;
   manipulating the target area of tissue relative to surrounding tissue at the first location; and
   adjusting a force vector exerted on the target area of tissue relative to surrounding tissue at the first location, the force vector having a direction of application and a magnitude.

2. The method of claim 1, wherein adjusting a force vector further comprises releasing the second element from the second location.

3. The method of claim 1, further including moving the second element toward a third location to increase the force vector exerted on the target area of tissue, the third location being spaced a greater distance from the first location than the distance of the second location from the first location.

4. The method of claim 1, further including adjusting the magnitude of the force vector by moving the first element and the second element relative to each other.

5. The method of claim 1, further including ejecting the first element from a holder and engaging the first element with the holder to move the first element to an open configuration to receive the target area of tissue.

6. The method of claim 5, wherein ejecting the first element from the holder further comprises moving the first element from the holder to move the first element to a closed configuration to anchor the first element to the target area of tissue and disengaging the first element from the holder.

7. The method of claim 1, wherein the first location and the second location are on the same tissue.

8. The method of claim 1, further comprising deploying the second element at the second location before extending the coupling element between the first element and the second element.

9. The method of claim 1, further comprising moving the second end of the coupling element from the second location to a third location spaced apart from the second location.

10. The method of claim 1, wherein the first element engages tissue at the first location to anchor the first end of the coupling element to the target area of tissue, and the second element engages tissue at the second location to anchor the second end of the coupling element at the second location.

11. The method of claim 1, wherein manipulating the target area of tissue further comprises cutting the target area of tissue.

12. A tissue retraction system, comprising:
- a stretchable tether having a first end and a second end;
- a first anchor having a fastener configured to engage tissue, the first end of the stretchable tether being directly coupled to the first anchor;
- a second anchor engageable with the second end of the stretchable tether; and
- an engagement element comprising a loop at the second end of the stretchable tether, the second anchor engageable with the loop.

13. The tissue retraction system according to claim 12, wherein at least one of the first anchor and the second anchor is a tissue clip having jaws.

14. The tissue retraction system according to claim 12, wherein the stretchable tether and the first anchor are deployable separately from the second anchor.

15. The tissue retraction system of claim 12, wherein the stretchable tether comprises a rubber band including at least one loop in addition to the loop of the engagement element.

16. The tissue retraction system of claim 12, wherein the stretchable tether comprises a rubber band including at least one loop.

17. A method comprising:
- anchoring a first end of a tether to a target area of tissue at a first location on a tissue and anchoring a second end of a tether at a second location on the tissue spaced from the first location to impart a force vector on the target area; and
- moving the second end of the tether to a third location spaced from the second location and the first location to adjust the force vector on the target area.

18. The method of claim 17, wherein the second location and the third location are locations along the same tissue.

19. The method of claim 17, wherein the first end of the tether is anchored to the target area of tissue with a first anchoring element, and the second end of the tether is anchored at a second location with a second anchoring element, the method further comprising locating the second anchoring element at the second location before imparting a force vector on the target area of tissue via the tether.

* * * * *